United States Patent
Foster et al.

(10) Patent No.: US 9,637,525 B2
(45) Date of Patent: May 2, 2017

(54) TREATMENT OF MICROBIAL INFECTIONS

(71) Applicant: The Provost, Fellows and Scholars of the College of the Holy and Undivided Trinity of Queen Elizabeth near Dublin, Dublin (IE)

(72) Inventors: Timothy Foster, Dublin (IE); Judy Higgins, Dublin (IE); Elisabet Josefsson, Gothenburg (SE); Joan Geoghegan, Dublin (IE); Andrej Tarkowski, Gavle (SE)

(73) Assignee: THE PROVOST, FELLOWS AND SCHOLARS OF THE COLLEGE OF THE HOLY AND UNDIVIDED TRINITY OF QUEEN ELIZABETH, Dublin (IE)

(*) Notice: Subject to any disclaimer, the term of this patent is extended or adjusted under 35 U.S.C. 154(b) by 0 days.

(21) Appl. No.: 14/701,789

(22) Filed: May 1, 2015

(65) Prior Publication Data

US 2015/0232518 A1 Aug. 20, 2015

Related U.S. Application Data

(62) Division of application No. 12/865,336, filed as application No. PCT/EP2009/051033 on Jan. 29, 2009, now abandoned.

(30) Foreign Application Priority Data

Jan. 31, 2008 (GB) .................................. 0801768.3
Jan. 31, 2008 (IE) .................................. 2008/0070

(51) Int. Cl.
*A61K 39/00* (2006.01)
*A61K 39/02* (2006.01)
(Continued)

(52) U.S. Cl.
CPC .............. *C07K 14/31* (2013.01); *A61K 38/00* (2013.01); *A61K 39/00* (2013.01)

(58) Field of Classification Search
CPC ........ A61K 38/00; A61K 38/16; A61K 39/40; A61K 38/164; A61K 39/4038;
(Continued)

(56) References Cited

U.S. PATENT DOCUMENTS

| 6,008,341 A | 12/1999 | Foster et al. |
| 6,177,084 B1 | 1/2001 | Foster et al. |
| 2003/0087864 A1 | 5/2003 | Talbot et al. |

FOREIGN PATENT DOCUMENTS

| WO | 00/64925 A1 | 11/2000 | |
| WO | WO 00-64925 | * 11/2000 | ........... C07K 14/195 |
| WO | 2005/116064 A2 | 12/2005 | |

OTHER PUBLICATIONS

Deivanayagam et al., (The EMBO Journal. 2002. vol. 21(24):6660-6672).*

(Continued)

*Primary Examiner* — Ja'na Hines
(74) *Attorney, Agent, or Firm* — Hovey Williams LLP

(57) ABSTRACT

The present invention is directed to improved microbial antigen vaccines, pharmaceutical compositions, immunogenic compositions and antibodies and their use in the treatment of microbial infections, particularly those of bacterial origin, including Staphylococcal origin. Ideally, the present invention is directed to a recombinant staphylococcal MSCRAMM or MSCRAMM-like proteins, or fragment thereof, with reduced binding to its host ligand, for use in therapy.

19 Claims, 18 Drawing Sheets

(51) Int. Cl.
- A61K 39/38 (2006.01)
- A61K 39/085 (2006.01)
- C07K 14/31 (2006.01)
- A61K 38/00 (2006.01)

(58) Field of Classification Search
CPC ............... A61K 39/39; A61K 39/085; A61K 47/48346; A61K 47/48415; A61K 48/005; A61K 2039/55516
See application file for complete search history.

(56) References Cited

OTHER PUBLICATIONS

Jossefsson et al., (J. Infect Dis. 2001. 184: 1572-1580).*
Loughman et al., (Molecular Microbiology. 2005. vol. 57(3): 804-818).*
Arnau et al., "Current strategies for the use of affinity tags and tag removal for the purification of recombinant proteins", Protein Expression and Purification, 2006, vol. 48 Issue 1, pp. 1-13.
Jossefsson et al., "Protection Against Experimental *Staphylococcus aureus* Arthritis by Vaccination With Clumping Factor A, A novel Virulence Determinant", Journal of Infectious Diseases, University of Chicago Press Chicao, IL, 2001, vol. 184 No. 12, pp. 1572-1580.
O'Connel, D.P. et al. "The Fibrinogen-binding MSCRAMM (Clumping Factor) of *Staphylococcus aureus* Has a Ca2+-dependent inhibitory Site", The Journal of Biological Chemistry, vol. 273, No. 12, Mar. 1998, pp. 6821-6829.
Deivanayagam et al., "A novel variant of the immunoglobulin fold in surance adhesins of *Staphylococcus aureus*: Crystal structure of the fibrinogen-binding MSCRAMM, clumping factor A", The EMBO Journal 2002 vol. 21 No. 24, pp. 6660-6672.
O'Brien, et al. "Multiple mechanisms for the activation of human platelet aggregation by *Staphylococcus aureus*: roles for the clumping factors CfA and CifB, the serine-aspartate repeat protein SdrE and protein A", Molecular Microbiology, vol. 44, No. 4, Feb. 2002, pp. 1033-1044.
Palmqvist, et al., "Fibronectin-Binding Proteins and Fibrinogen-Binding Clumping Factors Play Distinct Roles in Staphylococcal Arthritis and Systemic Inflammatio", the Journal of Infectious Diseases, vol. 191, Jan. 2005, pp. 791-798.
McDevitt, et al., "Molecular characterization of the clumping factor (fibrinogen receptor) of *Staphylococcus aureus*", Molecular Microbiology, vol. 11, No. 2, 1994, pp. 237-248.
Chambers, H.F., "Methicillin-resistant staphylococci", Clinical Microbiology Reviews, vol. 1, No. 2, Apr. 1988, pp. 173-186.
Duthie, et al., "Staphylococcal Coagulase: Mode of Action and Antigenicity", J. Gen. Microbiol., vol. 6, 1952, pp. 95-107.
McDevitt, et al., "Characterization of the interaction between the *Staphylococcus aureus* clumping factor (CiFA) and fibrinogen", Euro. J. Biochem., vol. 247, 1997, pp. 416-424.
Kreiswirth, et al., "The toxic shock syndrome exotoxin structural gene is not detectably transmitted by a prophage", Nature, vol. 305, Oct. 1983, pp. 709-712.
Bowden, et. al., "Evidence for the 'Dock, Lock, and Latch' Ligand Binding Mechanism of the Staphylococcal Microbial Surface Component Recognizing Adhesive Matrix Molecules (MSCRAMM) SdrG", The Journal of Biological Chemistry, vol. 282, No. 1, Jan. 2008, pp. 638-647.
Bremell, et al., "Histopathological and serological progression of experimental *Staphylococcus aureus* arthritis", Infection and Immunity, vol. 60, No. 7, Jul. 1992, pp. 2976-2985.
Bremell, et al., "Experimental *Staphylococcus aureus* arthritis in mice", Infection and Immunity, vol. 59, No. 8, Aug. 1991, pp. 2615-2623.

Patti, et al., "MSCRAMM-Mediated Adherence of Microorganisms to Host Tissues", Annu. Rev. Microbiol, vol. 48, 1994, pp. 585-617.
Foster, T.J., "Molecular Genetic Analysis of Staphylococcal Virulence", Methods in Microbiology, Academic Press, Lindon, vol. 27, 1998, pp. 433-454.
Higgins, et al., "Clumping factor A of *Staphylococcus aureus* inhibits phagocytosis by human polymorphonuclear leucocytes", FEMS Microbiol Lett, vol. 258, Apr. 2006, pp. 290-296.
Palmqvist, et al., "Expression of staphylococcal clumping factor A impedes macrophage phagocytosis", Microbes and Infection, vol. 6, 2004, pp. 188-195.
Peacock, et al., "Virulent Combinations of Adhesin and Toxin Genes in Natural Populations of *Staphylococcus aureus*", Infection and Immunity, vol. 70, No. 9, Sep. 2002, pp. 4987-4996.
Pilpa, et al., "Solution Structure of the NEAT (NEAr Transporter) Domain from IsdH/HarA: the Human Hemoglobin Receptor in *Staphylococcus aureus*", J. Mol. Biol., vol. 30, 2006, pp. 435-447.
Ponnuraj, et al., "A 'dock, lock, and latch' structural Model for a Staphylococcal Adhesin Binding to Fibrinogen", Cell, vol. 115, Oct. 2008, pp. 217-228.
Sakiniene, et al., "Complement depletion aggravates *Staphylococcus aureus* septicaemia and septic arthritis", Clin. Exp. Immunol., vol. 115, 1999, pp. 95-102.
Verdrengh, et al., "Role of neutrophils in experimental septicemia and septic arthritus induced by *Staphylococcus aureus*", Infection and Immunity, vol. 65, No. 7, Jul. 1997, pp. 2517-2521.
Loughman, et al., "Roles for fibrinogen, immunoglobulin and complement in platelet activation promoted by *Staphylococcus aureus* clumping factor A", Molecular Microbiology, 2005, vol. 57 No. 3, pp. 804-818.
Hartford, et al., "Identification of Residues in the *Staphylococcus aureus* Fibrinogen-binding MSCRAMM Clumping Factor A (ClfA) That Are Important for Ligand Binding", Journal of Biological Chemistry, 2001, vol. 276 No. 4, pp. 2466-2473.
Mitchell, et al., "Characterization of the fibrinogen-binding surface protein Fbl of *Staphylococcus lugdunenesis*", Microbiology, 2004, vol. 150 pp. 3831-3841.
Hall, et al., "Characterization of a Protective Monoclonal Antibody Recognizing *Staphylococcus aureus* MSCRAMM Protein Clumping Factor A", Infection and Immunity, 2003, vol. 71 No. 12, pp. 6864-6870.
Miajlovic, et al., "Both complement and fibrinogen dependent mechanisms contribute to platelet aggregation mediated by *Staphylococcus aureus* clumping factor B", Infection and Immunity, vol. 75, No. 7, Jul. 2007, pp. 3335-3343.
Keane, et al., "Fibrinogen and elastin bind to the same region within the a domain of fibronectin binding protein A, an MSCRAMM of *Staphylococcus aureus*", Molecular Microbiology, vol. 63, No. 3, Feb. 2007, pp. 711-723.
Kean, et al., "The N-terminal a domain of *Staphylococcus aureus* fibronectin-binding protein A binds to tropoelastin", Biochemistry, vol. 46, No. 24, Jun. 2007, pp. 7226-7232.
Josefsson, et al., "Fibrinogen binding sites P336 and Y338 of clumping factor A are crucial for *Staphylococcus aureus* virulence", PLoS ONE, vol. 3, No. 5, 2008, p. e2206.
Liu, et al., "A segment of *Staphylococcus aureus* clumping factor A with fibrinogen-binding activity (ClfA 221-550) inhibits platelet-plug formation in mice", Thrombosis Research, Jan. 1, 2007, vol. 12, No. 2, pp. 183-191.
International Search Report received for PCT Patent Application No. PCT/EP2009/051033, mailed on Apr. 28, 2009, 6 pages.
Written Opinion received for PCT Patent Application No. PCT/EP2009/051033, mailed on Apr. 28, 2009, 5 pages.
European Search Report in related European Application Serial No. EP 16173940, mailed Dec. 7, 2016.

* cited by examiner wild-type ClfA A (N123) domain protein (rClfA) (SEQ ID No. 2)

```
agtgaaaatagtgttacgcaatctgatagcgcaagtaacgaaagcaaaagtaatgattcaagt
 S  E  N  S  V  T  Q  S  D  S  A  S  N  E  S  K  S  N  D  S  S
agcgttagtgctgcacctaaaacagacgacacaaacgtgagtgatactaaaacatcgtca
 S  V  S  A  A  P  K  T  D  D  T  N  V  S  D  T  K  T  S  S
aacactaataatggcgaaacgagtgtggcgcaaaatccagcacaacaggaaacgacacaa
 N  T  N  N  G  E  T  S  V  A  Q  N  P  A  Q  Q  E  T  T  Q
tcatcatcaacaaatgcaactacggaagaaacgccggtaactggtgaagctactactacg
 S  S  S  T  N  A  T  T  E  E  T  P  V  T  G  E  A  T  T  T
acaacgaatcaagctaatacaccggcaacaactcaatcaagcaatacaaatgcggaggaa
 T  T  N  Q  A  N  T  P  A  T  T  Q  S  S  N  T  N  A  E  E
ttagtgaatcaaacaagtaatgaaacgactttttaatgatactaatacagtatcatctgta
 L  V  N  Q  T  S  N  E  T  T  F  N  D  T  N  T  V  S  S  V
aattcacctcaaaattctacaaatgcggaaaatgtttcaacaacgcaagatacttcaact
 N  S  P  Q  N  S  T  N  A  E  N  V  S  T  T  Q  D  T  S  T
gaagcaacaccttcaaacaatgaatcagctccacagagtacagatgcaagtaataaagat
 E  A  T  P  S  N  N  E  S  A  P  Q  S  T  D  A  S  N  K  D
gtagttaatcaagcggttaatacaagtgcgcctagaatgagagcatttagtttagcggca
 V  V  N  Q  A  V  N  T  S  A  P  R  M  R  A  F  S  L  A  A
gtagctgcagatgcaccggcagctggcacagatattacgaatcagttgacgaatgtgaca
 V  A  A  D  A  P  A  A  G  T  D  I  T  N  Q  L  T  N  V  T
gttggtattgactctggtacgactgtgtatccgcaccaagcaggttatgtcaaactgaat
 V  G  I  D  S  G  T  T  V  Y  P  H  Q  A  G  Y  V  K  L  N
tatggttttcagtgcctaattctgctgttaaaggtgacacattcaaaataactgtacct
 Y  G  F  S  V  P  N  S  A  V  K  G  D  T  F  K  I  T  V  P
aaagaattaaacttaaatggtgtaacttcaactgctaaagtgccaccaattatggctgga
 K  E  L  N  L  N  G  V  T  S  T  A  K  V  P  P  I  M  A  G
gatcaagtattggcaaatggtgtaatcgatagtgatggtaatgttatttatacatttaca
 D  Q  V  L  A  N  G  V  I  D  S  D  G  N  V  I  Y  T  F  T
gactatgtaaatactaaagatgatgtaaaagcaactttgaccatgcccgcttatattgac
 D  Y  V  N  T  K  D  D  V  K  A  T  L  T  M  ?  A  ?  I  D
cctgaaaatgttaaaaagacaggtaatgtgacattggctactggcataggtagtacaaca
 P  E  N  V  K  K  T  G  N  V  T  L  A  T  G  I  G  S  T  T
gcaaacaaaacagtattagtagattatgaaaaatatggtaagttttataacttatctatt
 A  N  K  T  V  L  V  D  Y  E  K  Y  G  K  F  Y  N  L  S  I
aaaggtacaattgaccaaatcgataaaacaaataatacgtatcgtcagacaatttatgtc
 K  G  T  I  D  Q  I  D  K  T  N  N  T  Y  R  Q  T  I  Y  V
aatccaagtggagataacgttattgcgccggttttaacaggtaatttaaaaccaaatacg
 N  P  S  G  D  N  V  I  A  P  V  L  T  G  N  L  K  P  N  T
gatagtaatgcattaatagatcagcaaaatacaagtattaaagtatataaagtagataat
 D  S  N  A  L  I  D  Q  Q  N  T  S  I  K  V  Y  K  V  D  N
gcagctgatttatctgaaagttactttgtgaatccagaaaactttgaggatgtcactaat
 A  A  D  L  S  E  S  Y  F  V  N  P  E  N  F  E  D  V  T  N
agtgtgaatattacattcccaaatccaaatcaatataaagtagagtttaatacgcctgat
 S  V  N  I  T  F  P  N  P  N  Q  Y  K  V  E  F  N  T  P  D
gatcaaattacaacaccgtatatagtagttgttaatggtcatattgatccgaatagcaaa
 D  Q  I  T  T  P  Y  I  V  V  N  G  H  I  D  P  N  S  K
ggtgatttagctttacgttcaactttatatgggtataactcgaatataatttggcgctct
 G  D  L  A  L  R  S  T  L  Y  G  Y  N  S  N  I  I  W  R  S
atgtcatgggacaacgaagtagcatttaataacggatcaggttctggtgacggtatcgat
 M  S  W  D  N  E  V  A  F  N  N  G  S  G  S  G  D  G  I  D
aaaccagttgttcctgaacaacctgatgagcctggtgaaattgaaccaattccagag
 K  P  V  V  P  E  Q  P  D  E  P  G  E  I  E  P  I  P  E
```

Fig. 10

TREATMENT OF MICROBIAL INFECTIONS

CROSS-REFERENCE TO RELATED APPLICATIONS

The present application is a divisional of U.S. patent application Ser. No. 12/865,336, which is the U.S. National Stage of International Patent Application No. PCT/EP2009/051033, filed Jan. 29, 2009, incorporated by reference herein in their entireties, and which claim priority to Ireland application No. 2008/0070, filed Jan. 31, 2008, and Great Britain application No. 0801768.3, filed Jan. 31, 2008.

SEQUENCE LISTING

The following application contains a sequence listing in computer readable format (CRF), submitted as a text file in ASCII format. The content of the CRF is hereby incorporated by reference.

INTRODUCTION

The present invention relates to improved microbial antigen vaccines, pharmaceutical compositions, immunogenic compositions and antibodies and their use in the treatment of microbial infections, particularly those of bacterial origin, including Staphylococcal origin.

Multiple drug resistance (MDR) is an increasing problem amongst gram positive bacteria, particularly in hospitals. The widespread use of antibiotics and other agents to treat bacterial infections has led to the rapid development of bacteria resistant to the agents and many bacteria have multiple drug resistance. Thus, there is now a need to provided improved therapies for dealing with such drug resistant infections.

Staphylococci are Gram-positive bacteria of spherical shape, usually arranged in grape-like irregular clusters. Some are members of the normal flora of the skin and mucous membranes of humans, others cause suppuration, abscess formation, a variety of pyogenic infections, and even fatal septicaemia. Pathogenic staphylococci often hemolyze blood, coagulate plasma, and produce a variety of extracellular enzymes and toxins.

The genus Staphylococcus has at least 30 species. The three main species of clinical importance are Staphylococcus aureus, Staphylococcus epidermidis, and Staphylococcus saprophyticus. Staphylococcus aureus is coagulase-positive, which differentiates it from the other species. S. aureus is a major pathogen for humans. Almost every person has some type of S. aureus infection during a lifetime, ranging in severity from food poisoning or minor skin infections to severe life-threatening infections. The coagulase-negative staphylococci are normal human flora which sometimes cause infection, often associated with implanted devices, especially in very young, old and immunocompromised patients. Approximately 75% of the infections caused by coagulase-negative staphylococci are due to S. epidermidis. Infections due to Staphylococcus warneri, Staphylococcus hominis, and other species are less common. S. saprophyticus is a relatively common cause of urinary tract infections in young women. Staphylococci produce catalase, which differentiates them from the streptococci. S. lugdunensis is also relevant in a clinical and is present in approximately 5 to 10% of cases of infective endocarditis.

S. aureus colonization of the articular cartilage, of which collagen is a major component, within the joint space appears to be an important factor contributing to the development of septic arthritis. Hematogenously acquired bacterial arthritis remains a serious medical problem. This rapidly progressive and highly destructive joint disease is difficult to eradicate. Typically, less than 50% of the infected patients fail to recover without serious joint damage. S. aureus is the predominant pathogen isolated from adult patients with hematogenous and secondary osteomyelitis.

In hospitalized patients, Staphylococcus bacteria such as S. aureus are a major cause of infection. Initial localized infections of wounds or indwelling medical devices can lead to more serious invasive infections such as septicaemia, osteomyelitis, mastitis and endocarditis. In infections associated with medical devices, plastic and metal surfaces become coated with host plasma and matrix proteins such as fibrinogen and fibronectin shortly after implantation. This ability of S. aureus and other staphylococcal bacteria to adhere to these proteins is essential to the initiation of infection. Vascular grafts, intravenous catheters, artificial heart valves, and cardiac assist devices are thrombogenic and prone to bacterial colonization. Of the staphylococcal bacteria, S. aureus is generally the most damaging pathogen of such infections.

A significant increase in S. aureus isolates that exhibit resistance to most of the antibiotics currently available to treat infections has been observed in hospitals throughout the world. The development of penicillin to combat S. aureus was a major advance in infection control and treatment. Unfortunately, penicillin-resistant organisms quickly emerged and the need for new antibiotics was paramount. With the introduction of every new antibiotic, S. aureus has been able to counter with β-lactamases, altered penicillin-binding proteins, and mutated cell membrane proteins allowing the bacterium to persist. Consequently, methicillin-resistant S. aureus (MRSA) and multidrug resistant organisms have emerged and established major footholds in hospitals and nursing homes around the world (Chambers, H. F., Clin Microbiol Rev, 1:173, 1988; and Mulligan, M. E., et al., Am J Med, 94:313, 1993). Today, almost half of the staphylococcal strains causing nosocomial infections are resistant to all antibiotics except vancomycin, and it appears to be only a matter of time before vancomycin will become ineffective as well.

Thus, there remains a very strong and rapidly growing need for therapeutics to treat infections from staphylococci such as S. aureus which are effective against antibiotic resistant strains of the bacteria.

In gram positive pathogens, such as Staphylococci, Streptococci and Enterococci, proteins, called adhesins, mediate such infections, for example by promoting colonization, attachment to blood clots and traumatized tissue. These specific microbial surface adhesins are termed MSCRAMMs (microbial surface components recognizing adhesive matrix molecules) (Patti, J., et al., Ann Rev Microbiol, 48:585-617, 1994; Patti, J. and Hook, M., Cur Opin Cell Biol., 6:752-758, 1994). MSCRAMMs specifically recognize and bind to extracellular matrix (ECM) components, such as fibronectin, fibrinogen, collagen, and elastin. These MSCRAMMs are found in many gram positive pathogens and their amino acid sequences are related, they have similar modular design and common binding domain organization.

MSCRAMMs on the bacterial cell surface and ligands within the host tissue interact in a lock and key fashion resulting in the adherence of bacteria to the host. Adhesion is often required for bacterial survival and helps bacteria evade host defense mechanisms and antibiotic challenges. Once the bacteria have successfully adhered and colonized host tissues, their physiology is dramatically altered and damaging components such as toxins and enzymes are secreted. Moreover, the adherent bacteria often produce a biofilm and quickly become resistant to the killing effect of most antibiotics.

A bacterium can express MSCRAMMs that recognize a variety of matrix proteins. Ligand-binding sites in MSCRAMMs appear to be defined by relatively short contiguous stretches of amino acid sequences (motifs). Because a similar motif can be found in several different species of bacteria, it appears as though these functional motifs are subjected to interspecies transfer (Patti and Hook, *Cur Opin Cell Biol*, 6:752-758, 1994). In addition, a single MSCRAMM can sometimes bind several ECM ligands.

MSCRAMMs can mediate infection by binding to proteins including Fibrinogen (Fg) and/or Fibronectin (Fn) etc. Fibrinogen and Fibronectin are proteins found in blood plasma and play key roles in hemostasis and coagulation.

Fibrinogen is composed of six polypeptide chains, two Aα, two Bβ and two γ-chains. The C-terminal part of the γ-chain is biologically important and interacts with the platelet integrin during platelet adherence and aggregation. It is this region which is also targeted by *Staphylococcus aureus* resulting in Fibrinogen-dependant cell clumping and tissue adherence.

*Staphylococcus aureus* has several surface expressed proteins which stimulate platelet activation and aggregation. The *Staphylococcus aureus* MSCRAMM proteins include but are not limited to the following:

Fibrinogen binding protein clumping factor A (ClfA);

Fibrinogen binding protein clumping factor B (ClfB);

Fibronectin-fibrinogen binding protein A (FnBPA);

Fibronectin-fibrinogen binding protein B (FnBPB); and

*S. aureus* surface proteins SasA, SasG, SasK etc.

Table 1 below outlines a selection of various *Staphylococcus aureus* cell wall-anchored surface proteins.

TABLE 1

| Surface protein | aa[a] | Ligand(s)[b] | Motif[c] | Sortase[d] |
|---|---|---|---|---|
| Protein A (Spa) | 508 | Immunoglobulin, von Willebrand Factor, TNFR[e] | LPETG | A |
| Fibronectin binding protein A (FnbpA) | 1,018 | Fibronectin, fibrinogen, elastin | LPETG | A |
| Fibronectin binding protein B (FnbpB) | 914 | Fibronectin, fibrinogen, elastin | LPETG | A |
| Clumping factor A (ClfA) | 933 | Fibrinogen, complement factor I | LPDTG | A |
| Clumping factor B (ClfB) | 913 | Fibrinogen, cytokeratin 10 | LPETG | A |
| Collagen adhesion (Cna) | 1,183 | Collagen | LPKTG | A |
| SdrC | 947 | Unknown | LPETG | A |
| SdrD | 1,315 | Unknown | LPETG | A |
| SdrE | 1,166 | Unknown | LPETG | A |
| Pls | 1,637 | Unknown | LPDTG | A |
| SasA | 2,261 | Unknown | LPDTG | A |
| SasB | 937 | Unknown | LPDTG | A |
| SasC | 2,186 | Unknown | LPNTG | A |
| SasD | 241 | Unknown | LPAAG | A |
| SasE/IsdA | 354 | Heme[f] | LPKTG | A |
| SasF | 637 | Unknown | LPKAG | A |
| SasG/Aap | 1,117 | Unknown[g] | LPKTG | A |
| SasH | 308 | Unknown | LPKTG | A |
| SasI/HarA/IsdH | 895 | Haptoglobin | LPKTG | A |

TABLE 1-continued

| Surface protein | aa[a] | Ligand(s)[b] | Motif[c] | Sortase[d] |
|---|---|---|---|---|
| SasJ/IsdB | 645 | Hemoglobin, heme | LPQTG | A |
| SasK | 211 | Unknown | LPKTG | A |
| IsdC | 227 | Heme | NPQTN | B |

[a]aa, protein length in amino acids.
[b]Molecular component(s) recognized and bound by protein.
[c]Consensus motif recognized by sortase and present in C-terminal cell wall sorting signal.
[d]Sortase for which cell wall surface protein is substrate.
[e]TNFR, tumor necrosis factor receptor
[f]also binds to proteins in desquamated epithelial cell. Promotes resistance to bactericidal lipids and lactoferrin
[g]also binds to desquamated nasal epithelial cells. Involved in biofilm formation.

Other Staphylococcal bacteria express surface expressed proteins (MSCRAMMs) which are similar to the clumping factors or binding proteins listed above. These include but are not limited to:

SdrF, SdrG and SdrH from *S. epidermidis* wherein SdrG/F have been shown to bind fibrinogen and collagen.

Fbl from *Staphylococcus lugdunensis* is a fibrinogen-binding protein. Fbl is a member of the Sdr-family, a group of staphylococcal cell surface proteins containing a characteristic serine-aspartate repeat region. The fibrinogen-binding domain of Fbl has been mapped to 313 amino acids, and shows 62% identity to the corresponding region in clumping factor A (ClfA) from *Staphylococcus aureus*.

Other ligand-binding proteins/adhesins include Isd proteins (iron-regulated surface determinants), which although all of them are not MSCRAMMs per se (e.g. IsdB and IsdH) promote adhesion of bacteria to extracellular matrix components and are referred to herein as "MSCRAMM-like proteins". It is known that IsdA promotes adhesion to squamous cells, and has weak affinity for fibrinogen and fibronectin, so may technically be defined as an MSCRAMM.

Clumping factor A (ClfA) was the first Fibrinogen γ-chain-binding *S. aureus* adhesin identified. Fibronectin-fibrinogen binding protein A (FnBPA) and Fibronectin-fibrinogen binding protein B (FnBPB) were subsequently recognized as bi-functional proteins found to bind the same C-terminal peptide segment in the γ-chain of Fg. ClfA and FnBPs have structural features that are common to all cell-wall anchored proteins expressed in Gram-positive bacteria, including ClfB.

Clumping factor A (ClfA), for example, is a surface located protein of *Staphylococcus aureus*. ClfA is an important virulence factor of *S. aureus*. It contributes to the pathogenesis of septic arthritis and endocarditis. ClfA is the archetype of a family of surface-associated proteins with similar structural/modular organization, including but not limited to ClfB, SdrD, SdrE etc.

ClfA contains a 520 amino acid N-terminal A domain (the Fibrinogen Binding Region), which comprises three separately folded subdomains N1, N2 and N3. The A domain is followed by a serine-aspartate dipeptide repeat region and a cell wall- and membrane-spanning region, which contains the LPDTG-motif for sortase-promoted anchoring to the cell wall. ClfA is present in practically all *S. aureus* strains (Peacock S J, Moore C E, Justice A, Kantzanou M, Story L, Mackie K, O'Neill G, Day N P J (2002) Virulent combinations of adhesin and toxin genes in natural populations of *Staphylococcus aureus*. *Infect Immun* 70:4987-4996). It binds to the C-terminus of the γ-chain of fibrinogen, and is thereby able to induce clumping of bacteria in fibrinogen solution (McDevitt D, Nanavaty T, House-Pompeo K, Bell E, Turner N, McEntire L, Foster T, Höök M (1997) Characterization of the interaction between the *Staphylococcus aureus* clumping factor (ClfA) and fibrinogen. *Eur J Biochem* 247:416-424 and McDevitt D, Francois P, Vaudaux P, Foster T J (1994) Molecular characterization of the clumping factor (fibrinogen receptor) of *Staphylococcus aureus*. *Mol Microbiol* 11:237-248).

3D Structural analysis of ClfA and the related fibrinogen-binding proteins SdrG and ClfB has revealed that the ligand-binding A domain in all these related proteins are all composed of three subdomains N1, N2 and N3, with residues 221-559 corresponding to Regions N2-N3 being the smallest truncate that retains the ability to bind fibrinogen. It has been found that amino acid residues 532 to 538 correspond to the latching peptide region of ClfA. Each subdomain comprises nine β-strands that form a novel IgG-type fold. The fibrinogen γ-chain peptide-binding site in these proteins is located in a hydrophobic groove at the junction between N2 and N3. It has been found that there is significant structural similarity between the 3d structure of these proteins, this is due to one or more of related amino acid sequence, similar modular design and common binding domain organization.

SdrC, SdrD, SdrE, FnBPA-A (all seven isoforms) and FnBPB-B (all seven isoforms) have similar modular organization, thus using PHYRE molecular modeling, these proteins would be expected to have the same 3D structure.

IsdA and IsdB do not have the same type of structure as Clf or Sdr proteins. They have a novel motif called NEAT which is involved in ligand binding. However, the NEAT motif is similar to the 3D structure of Clf or Sdr, in that is composed of a sandwich of beta strands (beta sandwich fold that consists of two five-stranded antiparallel beta sheets) and is a member of the Ig-superfamily (Pilpa et at "Solution Structure of the NEAT (NEAr Transported) Domain from IsdH/HarA: the Human Hemoglobin Receptor in *Staphylococcus aureus*" J. Mol. Biol. (2006) 360:435-447) The 3D structure of the NEAT motif of IsdH has been solved and residues in loop 1b-2 predicted.

Expression of ClfA on *S. aureus* hampers phagocytosis by both macrophages and neutrophils (Palmqvist N, Patti J M, Tarkowski A, Josefsson E (2004) Expression of staphylococcal clumping factor A impedes macrophage phagocytosis. *Microb Infect* 6:188-195 and Higgins J, Loughman A, van Kessel K P M, van Strijp J A G, Foster T J (2006) Clumping factor A of *Staphylococcus aureus* inhibits phagocytosis by human polymorphonuclear leukocytes. *FEMS Microbiol Lett* 258:290-296). In neutrophils this is due to both a fibrinogen-dependent mechanism and to a fibrinogen-independent mechanism. In contrast, platelets are activated by bacteria expressing ClfA through its interaction with GPIIb/IIIa leading to aggregation. This is most efficiently executed when fibrinogen is present, but there is also a fibrinogen-independent pathway for platelet activation (Loughman A, Fitzgerald J R, Brennan M P, Higgins J, Downer R, Cox D, Foster T J (2005) Roles of fibrinogen, immunoglobulin and complement in platelet activation promoted by *Staphylococcus aureus* clumping factor A. *Mol Microbiol* 57:804-818 and O'Brien L, Kerrigan S W, Kaw G., Hogan M., Penadés J., Litt D., Fitzgerald D. J., Foster T. J. & Cox D. (2002) Multiple mechanisms for the activation of human platelet aggregation by *Staphylococcus aureus*: roles for the clumping factors ClfA and ClfB, the serine-aspartate repeat protein SdrE and protein A. *Mol Microbiol* 44, 1033-1044).

ClfA is a virulence factor for induction of septic arthritis in mice (Josefsson E., Hartford O., O'Brien L, Patti J M, Foster T (2001) Protection against experimental *Staphylococcus aureus* arthritis by vaccination with clumping factor A, a novel virulence determinant. *J Infect Dis* 184:1572-1580). In addition, elimination of ClfA together with another fibrinogen binding protein ClfB protected against systemic inflammation at the early stages of infection (Palmqvist N, Foster T, Fitzgerald R, Josefsson E, Tarkowski A (2005) Fibronectin-binding proteins and fibrinogen-binding clumping factors play distinct roles in staphylococcal arthritis and systemic inflammation. *J Inf Dis* 191:791-798).

The *Staphylococcus aureus* fibrinogen binding protein ClfA has been isolated and characterized and is the subject of, for example, U.S. Pat. Nos. 6,008,341 and 6,177,084.

ClfA and ClfB have an identical structural (3D) organization and approximately 27% amino acid identity. FnBPA has an approximately 25% amino acid identity to ClfA.

At present there are no MSCRAMM based vaccines approved and on the market. Veronate®, a donor-selected staphylococcal human immune globulin intravenous (IGIV) targeting ClfA and SdrG, performed poorly in phase III clinical trials and was withdrawn from trials. It is currently being re-evaluated to determine whether it is a viable treatment for Staphylococcal infections.

WO 2005/116064 is directed to FnBPA, which is a multifunctional binding protein of *S. aureus*. The N-terminal A domain of FnBPA resembles ClfA and has been found to bind fibrinogen. However, the C-terminal BCD domains of FnBPA bind fibronectin, hence, FnBPA is a bifunctional MSCRAMM.

WO 2005/116064 is based on the finding that in the presence of transglutaminase, covalent linkages are formed between the bacterial adhesin FnBPA and the host protein fibronectin, rendering the association much stronger and essentially irreversible. Fibrinogen is a major component (~3 mg/ml) in blood where it serves as the final target of the coagulation cascade. Fibronectin is less abundant, ~0.3 mg/ml or one molecule of Fn for every 10-15 of fibrinogen. Fibrinogen and fibronectin are not thought to be associated in blood where they circulate independently.

Importantly, WO 2005/116064 specifically relates to Factor XIIIa-catalyzed covalent cross-linking. WO 2005/116064 isolates multiple mutants in a recombinant FnBPA where residues with positively charged side chains (i.e. transglutaminase substrates) were altered. Furthermore, WO 2005/116064 is directed to mutants which have altered covalent fibronectin not fibrinogen binding properties only. Additionally, this document does not demonstrate experimentally whether the binding of the mutant protein to the ligand is reduced and does not provide any supporting immunogenicity data.

Thus, in view of the prevalence of multiple drug resistance in gram positive bacteria and the lack of successful therapies and vaccines for these multi-drug resistant bacteria, any alternative therapy which can deal with such bacterial infections without using antibiotics will be of significant value.

Furthermore, any improvements in efficacy over any known treatments or vaccines will be of particular importance, especially in a clinical setting.

Thus, the present invention is directed to providing an alternative and improved therapy for such treating such bacterial infections.

STATEMENT OF THE INVENTION

According to a first general aspect of the invention, there is provided a recombinant staphylococcal MSCRAMM or MSCRAMM-like protein, or fragment thereof, with reduced binding to its host ligand, for use in therapy.

According to a preferred embodiment, there is provided a recombinant staphylococcal fibrinogen binding MSCRAMM protein, or fragment thereof comprising at least part of the fibrinogen binding region, without the ability to bind fibrinogen for use in therapy.

According to a second aspect of the invention, there is provided a method of inducing an immune response in an individual and/or treating a patient having a microbial infection, comprising administering to the individual a recombinant staphylococcal MSCRAMM or MSCRAMM-like protein, or fragment thereof, or vaccine comprising the recombinant staphylococcal MSCRAMM or MSCRAMM-like protein, or fragment thereof, with reduced binding to its host ligand.

According to a third aspect of the invention, there is provided a vaccine comprising a recombinant staphylococcal MSCRAMM protein, or fragment thereof, with reduced binding to its host ligand.

According to a fourth aspect of the invention, there is provided an antibody raised against a recombinant staphylococcal MSCRAMM or MSCRAMM-like protein, or fragment thereof, with reduced binding to its host ligand, preferably in the form of a hyperimmune serum.

According to a fifth aspect of the invention, there is provided an immunogenic pharmaceutical composition comprising a recombinant staphylococcal MSCRAMM or MSCRAMM-like protein, or fragment thereof, with reduced binding to its host ligand and a pharmaceutically acceptable adjuvant.

DETAILED DESCRIPTION

In this specification, the terms "adhesin", "MSCRAMM" and "cell-wall anchored proteins" will be understood to be interchangeable and cover all microbial derived ligand binding proteins. Ideally, these proteins bind fibrinogen, heme or haemoglobin, haptoglobin-haemoglobin, haemin, collagen and other such ligands. The term "MSCRAMM-like" proteins are intended to cover proteins or adhesins which have related amino acid sequences, similar modular design and/or common/similar binding domain organization to such MSCRAMM proteins, such as lsd proteins. Ideally, the MSCRAMM-like proteins have similar binding domain organization/modular design. Additionally, the MSCRAMM-like proteins may have at least 50%, preferably 60%, preferably 75%, more preferably 85%, even more preferably 95%, still more preferably 99% or more amino acid sequence identity with the MSCRAMM proteins.

It will also be understood that any of the percentage identities or homologies referred to in the specification are determined using available conventional methods over the entire/whole length of the sequence.

The term "micro-organism", "microbe", "microbial" or the like includes but is not limited to organisms including bacteria, fungi, viruses, yeasts and/or moulds.

The term "immunologically effective amount" covers those amounts which are capable of stimulating a B cell and/or T cell response.

According to a first general aspect of the invention, there is provided a recombinant staphylococcal MSCRAMM or MSCRAMM-like protein, or fragment thereof, comprising at least part of the ligand binding region, with reduced binding to its host ligand, for use in therapy. Such a recombinant protein may be used in the treatment of microbial infections, such as the treatment of sepsis, septic arthritis and/or endocarditis or other similar conditions or disease states. Such microbial infections may ideally be caused by Staphylococci or other similar micro-organisms.

According to one particular embodiment of this aspect of the invention, the recombinant MSCRAMM or MSCRAMM-like protein, or fragment thereof, has reduced or lacks the ability to non-covalently bind its host ligand.

Thus, it will be understood that the recombinant staphylococcal MSCRAMM or MSCRAMM-like protein, or fragment thereof, may have reduced binding with its host ligand or binding with the host ligand may be prevented.

It is postulated, according to the invention, that the non-covalent binding that takes place during binding, via Dock, Lock and Latching (DLL), of the MSCRAMM or MSCRAMM-like protein to its ligand may be reduced or prevented. It is established that the first step in binding of an MSCRAMM to its ligand involves a non-covalent interaction via the DLL model. These are the primary non-covalent MSCRAMM interactions with the ligand. The final stages in MSCRAMM-ligand binding involve covalent interactions. In this particular embodiment, the recombinant MSCRAMM or MSCRAMM-like protein, or fragment thereof, has reduced or lacks the ability to non-covalently bind its host ligand due to altered dock, lock and latching. One or more of the dock, lock or latching steps may be altered.

The DLL model was elucidated from the 3D structure of SdrG in complex with its ligand. ClfA has now been shown to act by a minor variation of the DLL mechanism (Ganech et al (2008) "A structural model of the *Staphylococcus aureus* Clfa-fibrinogen interaction opens new avenues for the design of anti-staphylococcal therapeutics". PloS Pathog 4(11); e1000226). The DLL model specifically relates to the non-covalent interactions involved in ligand binding. The DLL model is inferred for all other proteins of similar structural type (whether by amino acid similarity/homology or structural organization homology), including but not limited to MSCRAMM or MSCRAMM-like proteins.

In relation to MSCRAMMs ClfA/ClfB in particular, it has been found that the minimal ligand binding domain comprises Region A subregions N1 to N3, specifically subregions N2 and N3 which comprise a variant Dev-IgG Ig fold. The variant Dev-IgG Ig fold is new variant of the immunoglobulin motif also called the DE-variant. It is postulated that a hydrophobic pocket formed between the two DEv-IgG domains of ClfA/B is the ligand-binding site for the fibrinogen γ-chain. Essentially, the ligand binds to the hydrophobic groove separating N2 and N3. Specifically, during ligand binding the unfolded peptide component of the ligand inserts into the groove located between the N2 and N3 subdomains. The latching peptide at the C-terminus of subdomain N3 undergoes a conformational change and inserts between two beta strands in subdomain N2, thus, locking the ligand in place. Indeed, mutagenic substitution of residues Tyr256, Pro336, Tyr338 and Lys389 in the clumping factor, which are proposed to contact the terminal residues $^{408}$AGDV$^{411}$ of the fibrinogen γ-chain, resulted in proteins with no or markedly reduced affinity for fibrinogen. Further details of this specific embodiment are expanded on later.

Whilst these teachings relate to clumping factors, ClfA in particular, they are equally applicable to other MSCRAMMs and/or MSCRAMM-like proteins, which have similar modular binding domain organization and bind ligands in similar ways.

Thus, in order to provide recombinant staphylococcal MSCRAMM or MSCRAMM-like proteins, or fragment thereof, with reduced binding to its host ligand, the full length protein, ligand binding domain, minimal ligand binding domain or fragment thereof may be altered to reduce or prevent binding to its host ligand. Ideally, for ClfA/ClfB and other similar MSCRAMM or MSCRAMM-like proteins, Region A subregion N2 and N3, which ideally comprise a variant Dev-IgG Ig fold, may be altered to prevent or reduce binding to its host ligand. Such an alteration is designed to prevent the ligand binding to the hydrophobic groove separating minimal ligand binding domains needed for DLL.

Such alterations in the ligand binding domain may take place at the amino acid level, by amino acid substitution or deletion, using either the full length protein, ligand binding domain, minimal ligand binding domain or fragment thereof. It will be understood that proteins or fragments thereof with sufficiently high homology to the ligand binding protein may also be used. High homology as defined herein occurs when at least 50%, preferably 60%, preferably 70%, preferably 80%, more preferably 90%, even more preferably 95%, still more preferably 95% to 99%, still more preferably 99% or more of the nucleotides or match over the entire length of the DNA sequence or when used in connection with amino acid sequences when the amino acid sequences are not identical but produce a protein having the same functionality and activity. It will be understood that these comments about high homology may also relate to the 3D structure of the protein, i.e. modular binding domain organization.

It will be understood that the complete ligand binding protein, the ligand binding domain, the minimal ligand binding domain or a fragment thereof may be used.

The use of truncated proteins of the ligand binding protein such as the ligand binding domain, the minimal ligand binding domain, or the use of fragments thereof is advantageous for ease of manufacture and overcoming other problems such as unwanted cleavage of the protein. For example, the latching peptide, present in the minimal ligand binding domain, may be deleted/removed or altered. For example, the latching peptide in ClfA corresponds to Region A amino acids 532 to 538 and in ClfB to Region A amino acids 530-540 (Walsh et al (2004) JBC 279(49): 50691-50699). These residues may be altered, substituted or removed/deleted in order to prevent the ligand binding to the MSCRAMM via DLL. In this way the DLL "latching" of the MSCRAMM to its ligand is prevented. This "latching" occurs by way of a non-covalent interaction. In one embodiment, the latching peptide is removed in its entirety along with the remaining Region A C-terminal amino acid residues. According to another embodiment, the latching peptide region only is removed. According to yet another embodiment, the latching peptide region undergoes amino acid substitution to result in the reduction or prevention of ligand binding/latching. These comments are applicable to all MSCRAMM or MSCRAMM-like proteins with bind ligands by the DLL or similar models.

By altering the MSCRAMM or MSCRAMM-like protein in this manner, it is possible to provide a ligand binding protein without the ability to bind its ligand, which stimulates a greater immune response upon immunization than the wild type protein. Advantageously, this reduces systemic inflammation, thereby decreasing microbial virulence. Consequently, this altered ligand binding MSCRAMM or MSRAMM-like protein which lacks the ability to bind its ligand can be advantageously used in the treatment of microbial infections. Thus, these findings present a new and valuable vaccine/immunization therapeutic against bacterial infections which provides better results when compared to a vaccine or immunization therapeutic derived from the wild type protein.

According to one embodiment of the invention the ligand is heme, haemoglobin or fibrinogen. Other ligands may be contemplated such as haptoglobin-haemoglobin, haemoglobin, haemin, collagen etc.

According to another embodiment of the invention, the recombinant MSCRAMM protein is selected from
a fibrinogen binding protein; or
SdrD, SdrE, SdrG and/or SdrF.

Fibrinogen binding proteins have been expanded on above, and include but are not limited to ClfA, ClfB, FnBPA, FnBPB, Fbl, IsdA etc. It has been shown that SdrG/F bind collagen. Other MSCRAMMs include SasA, SasG, SasK and SdrH.

The recombinant MSCRAMM-like protein may be selected from
IsdA, IsdB, and/or IsdH.

Based on the findings from fibrinogen binding MSCRAMM ClfA, similar non-ligand binding mutants can be generated in for example the NEAT (NEAr Transporter) motif of Isd proteins including IsdH and IsdB. As expanded on above IsdA and IsdB do not have the same type of structure as the Clf or Sdr proteins. However, the NEAT motif in Isd is directly involved in ligand binding (haptoglobin-haemoglobin, haemoglobin, haemin), thus, alterations in the NEAT motif will prevent the host-ligand interation in the same way as altering the DLL or DLL like host-ligand interaction of Clf or Sdr. Many NEAT domain-containing proteins, including IsdA in *Staphylococcus aureus*, are implicated in haem binding. It is postulated that the haem-binding property of IsdA is contained within the NEAT domain. Crystal structures of the apo-IsdA NEAT domain and in complex with haem have revealed a clathrin adapter-like β-sandwich fold with a large hydrophobic haem-binding pocket. IsdB has two NEAT motifs and IsdA has one NEAT motif. Non-ligand binding mutants of Isd proteins may be isolated by altering the residues predicted for ligand binding, for example, by altering the residues between beta strands and/or hydrophobic pocket. Additionally, the NEAT motif may be altered to effect non-covalent host-ligand interactions.

According to another embodiment of this aspect of the invention, there is provided a method of inducing an immune response in an individual and/or treating a patient having a microbial infection, comprising administering to the individual a recombinant staphylococcal MSCRAMM or MSCRAMM-like protein, or fragment thereof, or vaccine comprising the recombinant staphylococcal MSCRAMM or MSCRAMM-like protein, or fragment thereof with reduced binding to its host ligand.

According to another embodiment of this aspect of the invention, there is provided a vaccine comprising a recombinant staphylococcal MSCRAMM or MSCRAMM-like protein, or fragment thereof, with reduced binding to its host ligand.

According to another embodiment of this aspect of the invention, there is provided an antibody raised against a recombinant staphylococcal MSCRAMM or MSCRAMM-like protein, or fragment thereof, with reduced binding to its host ligand, preferably in the form of a hyperimmune serum.

According to another embodiment of this aspect of the invention, there is provided an immunogenic pharmaceutical composition comprising a recombinant staphylococcal MSCRAMM or MSCRAMM-like protein, or fragment thereof, with reduced binding to its host ligand.

According to a preferred embodiment of the invention, there is provided a recombinant staphylococcal fibrinogen binding protein, or fragment thereof comprising at least the part of fibrinogen binding region, without the ability to bind fibrinogen for use in therapy.

It will be understood that the recombinant Staphylococcal fibrinogen binding protein, or fragment thereof, may be used in the treatment of microbial infections, preferably Staphylococci infections such as in the treatment of sepsis, septic arthritis and/or endocarditis or other similar conditions or disease states.

The fibrinogen binding region of the protein is altered so that it no longer binds fibrinogen. As stated above, the alteration may take place at the nucleotide or amino acid level. It will be understood that proteins or fragments thereof with sufficiently high homology to the fibrinogen binding protein may also be used. High homology as defined herein occurs when at least 50%, preferably 60%, preferably 70%, preferably 80%, more preferably 90%, even more preferably 95%, still more preferably 95% to 99%, still more preferably 99% of the nucleotides match over the entire length of the DNA sequence or when used in connection with amino acid sequences when the amino acid sequences are not identical but produce a protein having the same functionality and activity. It will be understood that these comments about high homology may also relate to the 3D structure of the protein.

It will be understood that the complete fibrinogen binding protein, the fibrinogen binding region, the minimal fibrinogen binding region, or a fragment thereof may be used. The use of truncated proteins or fragments thereof is advantageous for ease of manufacture and overcoming other problems such as unwanted cleavage of the protein. This is expanded on below.

Such fragments should ideally comprise at least part of the fibrinogen binding region of the MSCRAMM. The advantages of using a truncated protein or fragment thereof of the, comprising for example one or more subdomains of the ligand-fibrinogen binding region only, relate to the ability to purify the protein at high yields without degradation. The ClfA protein fibrinogen binding region, otherwise referred to as the A Region, comprises 3 subregions, N1, N2 and N3. Thus, the immunogenic fragment may comprise subregions N1, N2 and/or N3 of the ClfA A Region or a fragment thereof. Thus, for example, in relation to ClfA, the fragment may comprise one or more of subdomains of Region A, N1, N2 or N3. Ideally, N2 and N3 may be used as this truncate is less likely to undergo proteolysis (a protease cleavage site has been reported between N1 and N2 in ClfA and ClfB) and can be expressed at higher levels in *E. coli*. N2 and N3 are the minimal fibrinogen binding region of Clf proteins.

It will be understood that although the following discussion relates to the fibrinogen binding protein ClfA, that these comments are equally applicable to other MSCRAMMs, MSCRAMM-like proteins and in particular other fibrinogen binding proteins which are structurally similar either at an amino acid or protein structure level to ClfA, for example as ClfB, Fbl and SdrF/G (which also bind collagen). Furthermore, these teachings are applicable to FnBPA and FnBPB. Thus, although the following comments relate to fibrinogen binding proteins, they are equally applicable to other MSCRAMM or MSCRAMM-like proteins which bind ligands other than fibrinogen.

We have unexpectedly found that this altered fibrinogen binding protein, truncate or fragment thereof, without the ability to bind fibrinogen stimulates a greater immune response upon immunization than the wild type protein which binds to fibrinogen in the normal manner. Advantageously, this altered fibrinogen binding protein does not provoke systemic inflammation when expressed by *S. aureus*, thus, microbial virulence is decreased. Consequently, this altered protein which lacks the ability to bind fibrinogen can be advantageously used in the treatment of microbial infections. We have also found contrary to expectations that the protection effect of the altered fibrinogen binding protein is greater than the wild type protein. We have found that a pharmaceutical composition or vaccine comprising such an altered recombinant protein is more effective than a pharmaceutical composition or vaccine comprising the same recombinant protein in an unaltered (wild type) form, such as ClfA, ClfB, SdrG etc.

Thus, these findings present a new and valuable vaccine/immunization therapeutic against bacterial infections which provides better results when compared to the wild type protein when also used as a vaccine/immunization therapeutic.

It will be understood that the altered protein, whether MSCRAMM or MSCRAMM-like or fibrinogen or other ligand binding, may be used in the generation of antibodies, including monoclonal, polyclonal, chimeric, humanized antibodies or fragments thereof, for use in the treatment of such microbial infections. Compositions may then be provided which include such antibodies, such as a hyperimmune serum, and these compositions may be used in the treatment of patients infected with *Staphylococcus* infections.

Thus, the proteins or active fragments thereof may be used to inhibit the binding of Staphylococci to the extracellular matrix (ECM) and to prevent/treat Staphylococci infections in a patient.

Furthermore, the proteins or active fragments thereof, and antibodies to the proteins are useful in the treatment of infections from Staphylococcal infections, for the development of vaccines for active or passive vaccination, and when administered as a pharmaceutical composition to a wound or a medical device, both the proteins and antibodies are useful as blocking agents to prevent microbial infection. For example, these proteins or fragments thereof may be used in active vaccines, and the antibodies to these proteins in passive vaccines.

These vaccines and products described herein present a significant improvement over the prior art, which teaches the general use of MSCRAMMs to impart immunization, but does not teach the unexpected and improved vaccines or products described herein.

The preparation of proteins, DNA and antibodies are well known in the art and will not be described in detail herein. Conventional techniques are ideally used in the generation of these molecules. The invention will also be understood to cover nucleic acid constructs containing the nucleic acid or amino acid sequence of interest, recombinant host cells containing such nucleic acid constructs to express the protein of interest, and immunogenic compositions.

For administration, the protein composition may be dispersed in a sterile, isotonic saline solution or other pharmaceutically acceptable adjuvant.

It will be understood that the vaccine may be a DNA or protein vaccine.

Immunization may take place by the injection of DNA, protein or antibodies. Alternatively, an attenuated live organism that includes and expresses the DNA may be administered.

The amount of DNA, protein or antibodies that may be administered will depend on several mitigating factors, including dependence on the promoter strength, protein expression and immunogenicity of the expressed gene. These may be altered for each new application to obtain the desired immunologically effective amount required.

According to another embodiment of this invention, there is provided a method of inducing an immune response in an individual and/or treating a patient having a microbial infection, comprising administering to the individual a recombinant Staphylococcal fibrinogen binding protein, or fragment thereof comprising at least the fibrinogen binding region, without the ability to bind fibrinogen.

According to further preferred embodiment of the invention, there is provided a vaccine comprising a recombinant Staphylococcal fibrinogen binding protein, or fragment thereof comprising at least part of the fibrinogen binding region, without the ability to bind fibrinogen.

According to a still further preferred embodiment of the invention, there is provided an antibody raised against a recombinant Staphylococcal fibrinogen binding protein, or fragment thereof comprising at least part of the fibrinogen binding region, without the ability to bind fibrinogen, preferably in the form of a hyperimmune serum.

According to a yet further preferred embodiment of the invention, there is provided an immunogenic pharmaceutical composition comprising a recombinant Staphylococcal fibrinogen binding protein, or fragment thereof comprising at least part of the fibrinogen binding region, without the ability to bind fibrinogen and a pharmaceutically acceptable adjuvant.

Ideally, the recombinant Staphylococcal fibrinogen binding protein or fragment thereof is derived from S. aureus, S. epidermidis and/or S. lugdunensis.

The fibrinogen binding protein of these embodiments may be selected from one of the following Fbl, SdrF, and/or SdrG (which are also collagen binding). Alternatively, the fibrinogen binding protein may be selected from one of the following Fibrinogen binding protein clumping factor A (ClfA), Fibrinogen binding protein clumping factor B (ClfB), Fibronectin-fibrinogen binding protein A (FnBPA), Fibronectin-fibrinogen binding protein B (FnBPB). IsdA promotes adhesion has weak affinity for fibrinogen and fibronectin, so may technically be defined as a fibrinogen binding MSCRAMM.

It will be understood that nucleotide or amino acid substitutions or deletions within the fibrinogen binding region of such fibrinogen binding proteins result in a recombinant protein without the ability to bind fibrinogen.

ClfA-fibrinogen binding has been elucidated to occur by a dock, lock and latch (DLL) mechanism similar to that of SdrG. The DLL model was expanded on above. Region A of ClfA is responsible for the protein-ligand interaction. As shown in FIG. 11, the modular structure of several fibrinogen binding MSCRAMM are similar and all contain Region A similar to ClfA.

The fibrinogen γ-chain peptide-binding site is located in a hydrophobic groove at the junction between N2 and N3 of ClfA. Thus, the substitutions or deletions mentioned above are designed to alter the MSCRAMM protein-ligand interaction and prevent the non-covalent binding of ClfA to fibrinogen.

According to one specific embodiment of the present invention, the recombinant Staphylococcal fibrinogen binding protein is a fibrinogen binding-deficient mutant of ClfA. In this embodiment, Fibrinogen Binding Region A of ClfA is altered by any means (such as substitution or deletion mutations) so that it no longer binds fibrinogen.

Ideally, the fibrinogen binding protein is ClfA, however, ClfA bears 3D structural similarity to many other fibrinogen binding proteins. Thus, it will be understood that these comments relating to ClfA are equally applicable to other MSCRAMM fibrinogen binding proteins, including ClfB, FnBPA, FnBPB, Fbl, SdrG/F, IsdA etc. All of these proteins have similar 3D structures, thus, similar alterations/mutations to the fibrinogen binding region can be made to achieve the same results.

ClfA is a 993 amino acid protein, comprising a 520 amino acid fibrinogen binding domain (from amino acids 40 to 559). This fibrinogen binding domain is the N Terminal A domain comprising subregions N1, N2 and N3. The entire fibrinogen region spanning N1 to N3 from amino acid 40 to amino acid 559 may be used in the invention. Alternatively, a truncate of the N1 to N3 region may be used, e.g. 221 to 559 (the minimal fibrinogen binding region), 221 to 531 (the minimal fibrinogen region without the latching peptide and following residues) etc. Ideally, subregions N2 and N3, the minimal fibrinogen binding region, may be used which correspond to amino acid residues 221 to 559. Alternatively, a fragment of these subregions may be used.

It has been established that amino acid residues 221 to 559, covering the N2 and N3 regions, of ClfA play an important part in the binding to fibrinogen and are the minimal fibrinogen binding region. We also have unexpectedly found that mutation of amino acid residues in this region results in an expressed protein which can be recognized by the host immune defenses but lacks fibrinogen binding and hence, reduces the associated virulence. This region (the 339 amino acid fibrinogen binding domain) of ClfA has a specific 3D structure, a so-called DE-variant IgG fold, and is the minimum Fg-binding truncate which if altered (via substitution or deletion etc) can provide an improved therapy.

The alteration to result in the loss of fibrinogen binding activity may take place by substitution, addition or insertion or deletion at either the nucleotide or amino acid level. Ideally, the substitution negatively affects the 3D structure (e.g. of the a so-called DE-variant IgG fold) of the protein or fragment so it can no longer bind fibrinogen.

Ideally, the nucleotide or amino acid substitution reduces the non-covalent interaction with fibrinogen, preferably by preventing ligand binding to the hydrophobic pocket separating N2 and N3 of Region A of the fibrinogen binding protein. Alternatively, the latching peptide region corresponding to amino acids 532 to 538 may be altered by substitution or deleted to prevent ligand binding. Additionally, a truncate/fragment lacking the latching peptide region and optionally the remainder of the C-terminal protein residues, i.e. lacking amino acid residues 532 to 559, may be used.

According to one specific embodiment of this aspect of the invention, the fibrinogen binding-deficient mutant of ClfA may be constructed by exchanging amino acids $P_{336}$ for serine and/or $Y_{338}$ for aspartate, respectively. The choice of residues was based on the X-ray crystal structure of ClfA and the observation that individual changes to the proline or the tyrosine reduced binding affinity. Surprisingly, we found that this mutant ClfA protein (rClfA$P_{336}$S $Y_{338}$A) stimulated an immune response and can be used in the generation of a much more effective vaccine or antibody therapy. This substitution may take place in the full length fibrinogen binding protein, the fibrinogen binding region, the minimal fibrinogen binding region, or a fragment thereof.

According to another specific embodiment of this aspect of the invention, the fibrinogen binding-deficient mutant of ClfA may be constructed by exchanging amino acids $P_{336}$ for aspartate and/or $Y_{338}$ for serine, respectively. As with the previous embodiment, this mutant ClfA protein (rClfAP$_{336}$A Y$_{338}$S) can also be used in the generation of a much more effective vaccine or antibody therapy.

Alternatively, the alteration may be in the form of a deletion, comprising the fibrinogen binding region without the latching peptide sequence (amino acids 532 to 538), to result in a recombinant fibrinogen binding protein without the ability to non-covalently bind fibrinogen. In this embodiment, amino acid residues 221 to 531 of Region A of ClfA are used, which lack the latching peptide and following C-terminal residues. Alternatively, an amino acid substitution in the latching peptide amino acids 532 to 538 which prevents the DLL of the fibrinogen may be contemplated.

It is understood that all proteins in the Clf-Sdr family binds ligands by the DLL model. By modelling the 3D structure, it is possible to predict the latching peptide and make a truncate that lacks it, either in the full length (N1 to N3) or the minimal ligand binding truncate N2-N3, or a fragment thereof.

We found that these substitution rClfA proteins (whether deletion mutants, substitutions or truncates) reduced virulence and disease outcome, and surprisingly induced less systemic inflammation that the wild type protein.

Thus, immunization with these mutant proteins is expected to, based on the proteins tested, enhance the level of antibodies which recognized both the mutant and wild type protein and to provide for a greater immune response than the wild type protein.

Thus, ClfA which has been altered so that it no longer binds fibrinogen is a useful therapeutic candidate for active or passive immunization. In this way, the altered ClfA protein itself may be used as a vaccine or antibodies raised to this altered ClfA protein may be used. As above the vaccine may be a DNA or protein vaccine.

The following sequences outlined in the table below may be used in accordance with the invention.

| SEQ ID No | Description | Length | A Region |
|---|---|---|---|
| 1 | wt rClfA - full length aa sequence (Example 1) | 933 aa | — |
| 2 | wt rClfA A Region - full length DNA sequence (Example 1) | 1560 nucleotides | N1 to N3 |
| 3 | wt rClfA A Region - full length aa sequence (Example 1) | 520 aa | N1 to N3 |
| 4 | rClfAPYI A Region (Example 1) | 520 aa | N1 to N3 |
| 5 | rClfAPYII A Region (Example 1) | 520aa | N1 to N3 |
| 6 | wt rClfA A Region - full length aa sequence with additional N and C terminal residues[1] (Example 2) | 530aa | N1 to N3 |
| 7 | rClfAPYI A Region with additional N and C terminal residues[1] (Example 1) | 530aa | N1 to N3 |
| 8 | rClfAPYII A Region with additional N and C terminal residues[1] | 530aa | N1 to N3 |
| 9 | rClfA 221-559 (Example 2) | 339 aa | N2 and N3 |
| 10 | rClfA 221-559 with additional N and C terminal residues[1] (Example 2) | 349 aa | N2 and N3 |
| 11 | rClfA PY 221-559 (Example 2) | 339aa | N2 and N3 |
| 12 | rClfA PY 221-559 with additional N and C terminal residues[1] (Example 2) | 349aa | N2 and N3 |
| 13 | rClfA 221-531 (delta latch truncate) with additional N and C terminal residues[2] (Example 2) | 321aa | N2 and N3[3] |
| 14 | rClfAPY 221-531 (delta latch truncate) | 311 aa | N2 and N3[3] |

[1]Additional N residues (N-terminal extension (6 x His tag and additional residues) comprise 6 His residues, followed by Gly and Ser. Additional C terminal residues comprise Lys followed by Leu (other additional N and C terminal residues may be used - depending on the primer used or N/C terminal tags required)
[2] Additional N residues (6 x His tag and additional residues) comprise 6 His residues, followed by Gly and Ser. Additional C terminal residues comprise Arg followed by Ser (other additional N and C terminal residues may be used - depending on the primer used or N/C terminal tags required))
[3]without the latching peptide corresponding to aa residues 532 to 538 and remainder A Region C-terminal residues i.e. lacking amino acid residues 532 to 559.

Ideally, the recombinant Staphylococcal fibrinogen binding protein comprises the amino acid sequence according to any of SEQ ID Nos. 1 to 3 wherein residue $P_{336}$ and/or $Y_{338}$ are substituted with either serine and/or alanine, or a fragment thereof.

Alternatively, the fragment of the recombinant Staphylococcal fibrinogen binding protein comprises the amino acid sequence according to any of SEQ ID No. 4 to SEQ ID No. 14. SEQ ID NOs 4 and 5 correspond to the ClfA A domain N1, N2, N3 only, rClfA P$_{336}$S Y$_{338}$A and rClfA P$_{336}$A Y$_{338}$S respectively as outlined in the table above.

It is also postulated, based on the substitutions in the latch which were made in SdrG, that substitutions in the latch that are defective in the conformational change or beta strand complementation will also be defective in ligand binding. Thus, ideally, the substitutions are in amino acid residues 532 to 538 which correspond to the latching peptide and affect the ability of the peptide to undergo conformational change, or bind the ligand or both. Alternatively, the alteration may comprise removing the amino acid residues 532 to 538 (delta latch peptide) altogether, to give similar results. Additionally, a C-terminal truncation mutant lacking amino acid residues 532 to 559 (including the latching peptide residues) will also effect binding to the ligand.

However, it will also be contemplated that other amino acid residues could be substituted other than those specifically recited above. For example, Glu 526, Val 527, Tyr 256 and Lys 389 may be substituted to alter the fibrinogen binding properties of the protein or fragment thereof. Thus, any substitution which reduces binding ability may be contemplated. Ideally, such substitutions or deletions effect the hydrophobic pocket and associated mechanism for binding the ligand in the hydrophobic trench such as homologues Val527 in ClfA and N526 in ClfB. In ClfB, Q235 and N526 have been studied to shown to reduce binding. A similar study was done with FnBPA where N304 and F306 were shown to be important for Fg binding. Thus, mutations in these amino acid residues will affect ligand binding.

It will be understood that these comments are equally applicable to other fibrinogen binding proteins, such as ClfB, SdrG, FnBPA, FnBPB. Thus, the treatment (vaccine, antibody or pharmaceutical composition etc) may comprise the complete Fibrinogen Binding Region or a fragment thereof.

In the specification, the terms "comprise, comprises, comprised and comprising" or any variation thereof and the terms "include, includes, included and including" or any variation thereof are considered to be totally interchangeable and they should all be afforded the widest possible interpretation.

The invention is not limited to the embodiment hereinbefore described, but may be varied in both construction and detail within the scope of the claims.

The present invention will now be described with reference to the following non-limiting figures and examples.

FIGS. 1 to 15 show the results of Example 1.

FIG. 1 shows the severity of arthritis (A), measured as arthritic index, and weight loss (B) in mice inoculated with S. aureus strain Newman, and clfAPYI, clfAPYII, and clfA null mutants. $3.2 \times 10^6$-$6.0 \times 10^6$ cfu of S. aureus strains were inoculated. Data are presented as medians (squares or center lines), interquartile ranges (boxes), and 80% central ranges (whiskers). Data from three experiments are pooled. $N_{Newman}$=27-30, $N_{clfAPYI}$=30, $N_{clfAPYII}$=10, and $N_{clfA}$=16-20.

FIG. 2 shows the bacterial growth in kidneys in mice 7-8 days after inoculation with $3.2 \times 10^6$-$6.0 \times 10^6$ cfu of S. aureus strain Newman, and clfAPYI, clfAPYII, and clfA null mutants. Data are presented as cfu per kidney pair. Where no growth was detectable, the count was put to highest possible count according to what dilution was used. Data from three experiments are pooled. $N_{Newman}$=26, $N_{clfAPYI}$=30, $N_{clfAPYII}$=10, and $N_{clfA}$=15.

Figure 5:
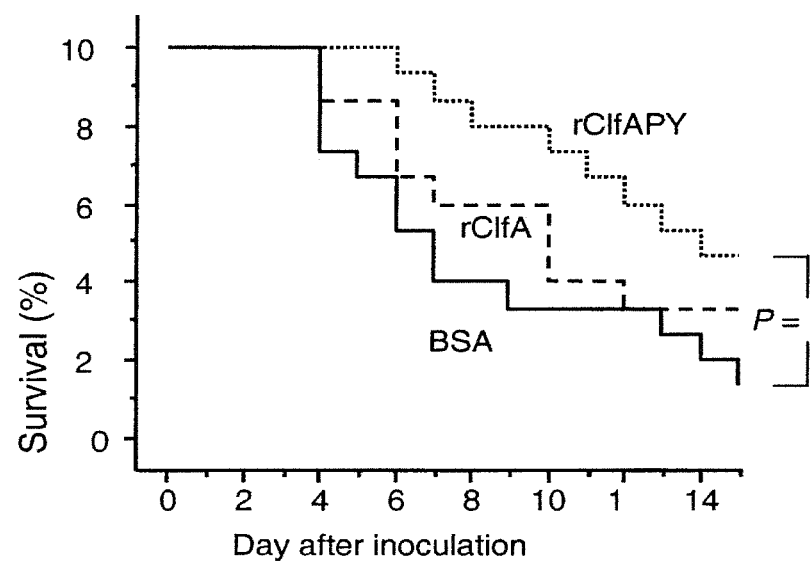

FIG. 5 shows the survival of mice immunized with BSA, recombinant ClfA or recombinant ClfAPY (i.e. ClfAPYI recombinant protein A domain) and inoculated with $2.3 \times 10^7$ cfu of S. aureus Newman. N=15 per group from start.

Figure 6:
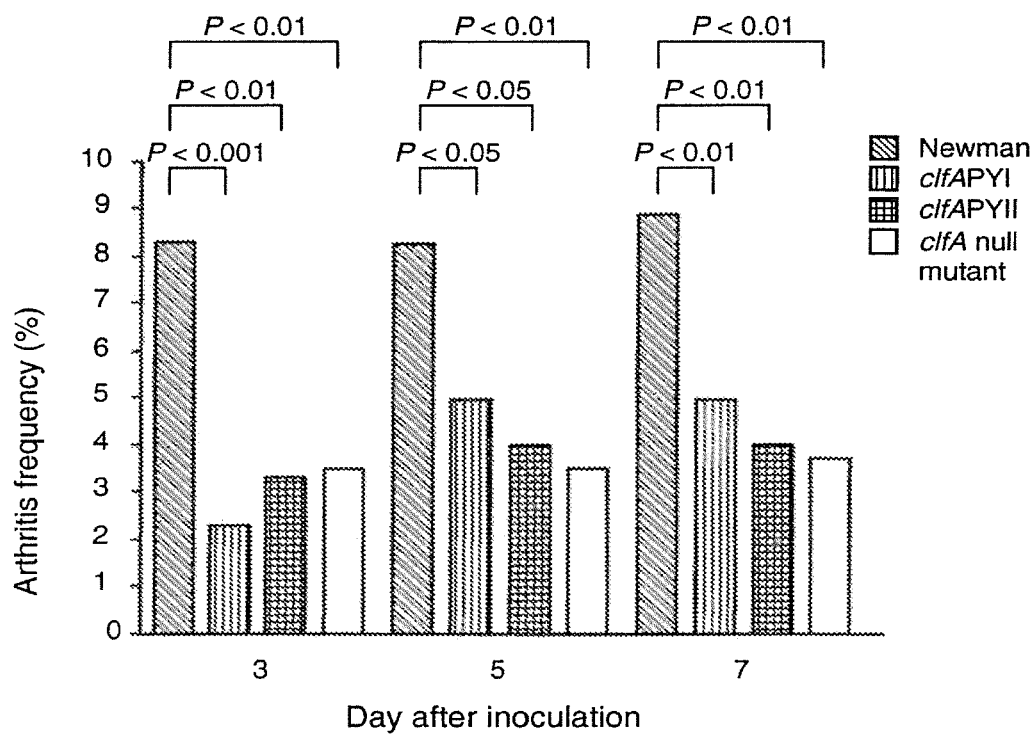

FIG. 6 shows the frequency of arthritic mice inoculated with $3.2 \times 10^6$-$6.0 \times 10^6$ cfu of S. aureus strain Newman wildtype, and clfAPYI, clfAPYII, and clfA null mutants. Data from three experiments are pooled. $N_{Newman}$=27-30, $N_{clfAPYI}$=30, $N_{clfAPYII}$=10, and $N_{clfA}$=16-20.

Figure 7:
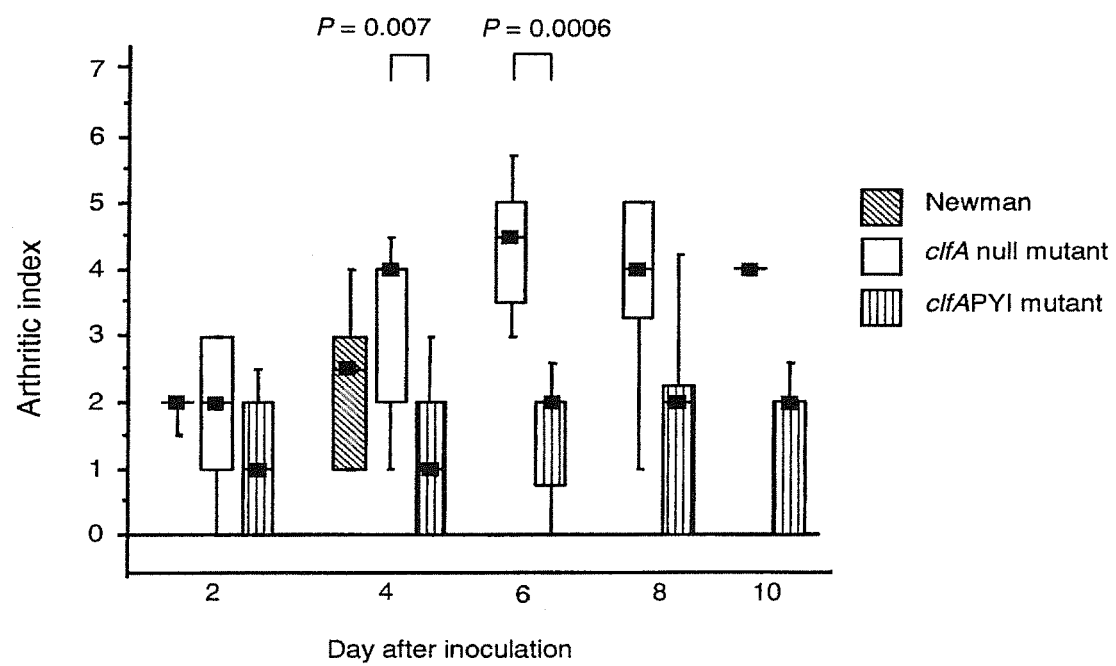

FIG. 7 shows the severity of arthritis measured as arthritic index in mice inoculated with 5.2, 5.1 or $3.3 \times 10^7$ cfu of S.aureus strain Newman wild-type, clfAPYI mutant or clfA null mutant, respectively. Data are presented as medians (squares), interquartile ranges (boxes), and 80% central ranges (whiskers). $N_{Newman}$=0-10, $N_{clfAPYI}$=9-10, and $N_{clfA}$=0-10.

Figure 8:
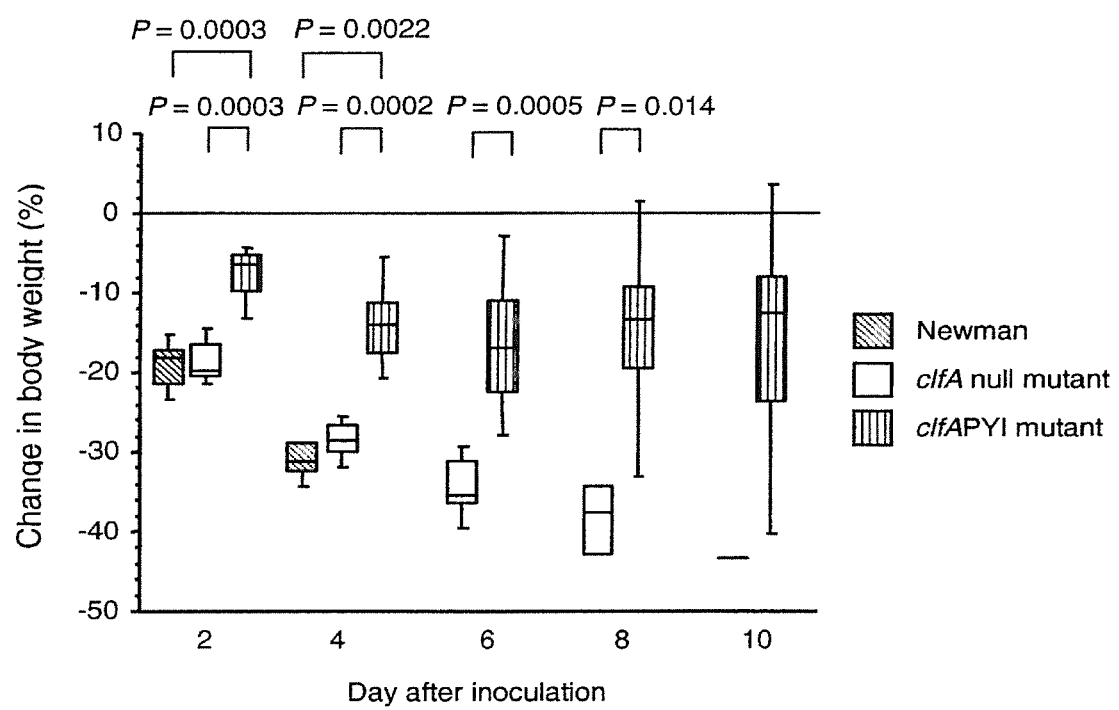

FIG. 8 shows the weight loss in mice inoculated with 5.2, 5.1 or $3.3 \times 10^7$ cfu of S.aureus strain Newman wild-type, clfAPYI mutant or clfA null mutant, respectively. Data are presented as medians (center line), interquartile ranges (boxes), and 80% central ranges (whiskers). $N_{Newman}$=0-10, $N_{clfAPYI}$=9-10, and $N_{clfA}$=0-10.

Figure 9:
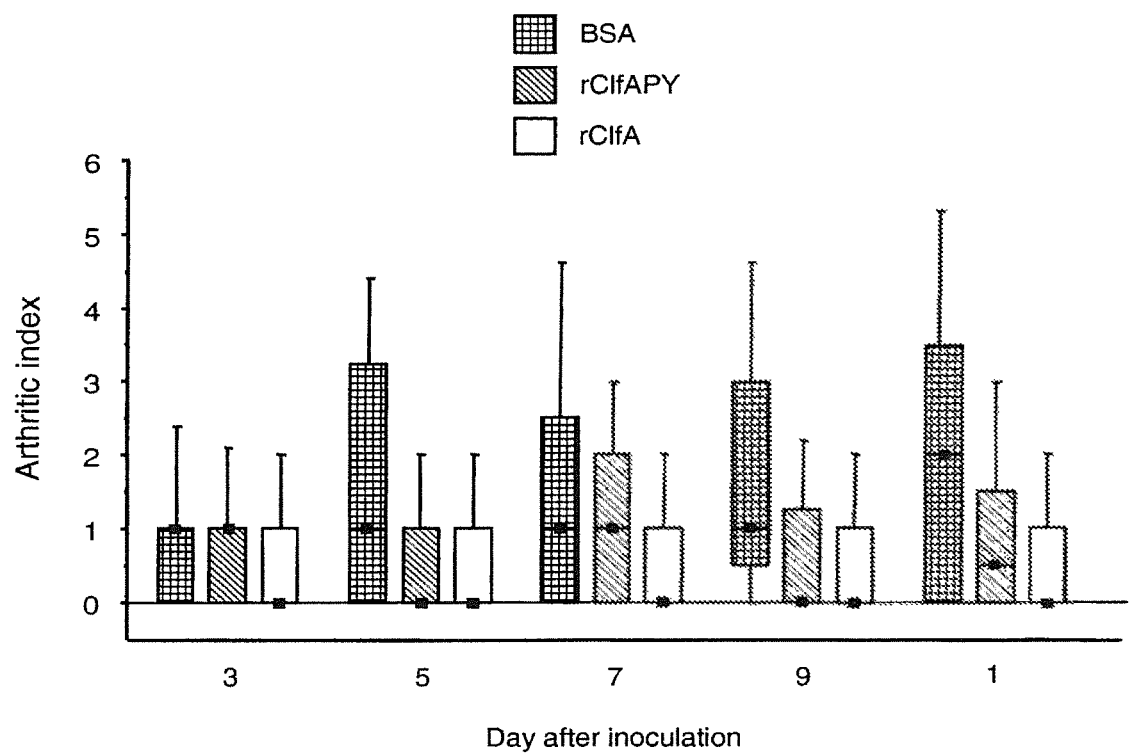

FIG. 9 shows the severity of arthritis measured as arthritic index in mice immunized with BSA, recombinant ClfA or recombinant ClfAPY (i.e. ClfAPYI recombinant protein A domain) and inoculated with $4.0 \times 10^6$ cfu of S. aureus Newman. Data are presented as medians (squares), interquartile ranges (boxes), and 80% central ranges (whiskers). $N_{BSA}$=14, $N_{clfAPY}$=14, and $N_{clfA}$=15 per group from start.

FIG. 10 gives the nucleotide and amino acid sequence of wild-type ClfA A domain protein (rClfA), domains N123 only, with the residues highlighted which are altered in the following examples ($P_{336}$ and $Y_{338}$) to give rise to rClfAPYI/II (SEQ ID No.3). It is this recombinant protein A domain which was used in vaccination in the following examples.

Figure 11:
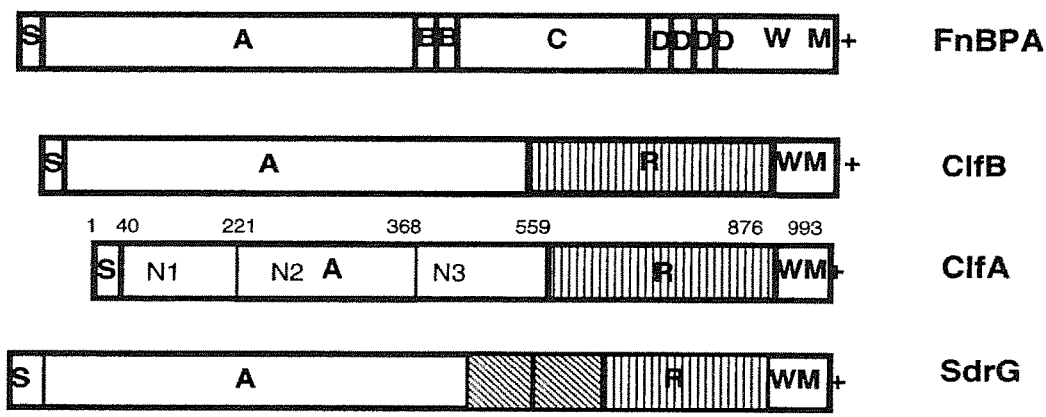

FIG. 11 shows an illustrative representation of the structure of FnBPA, ClfB, ClfA and SdrG proteins. Region A is the fibrinogen binding region, S is the signal sequence, W is the cell wall spanning domain, M is the membrane anchor including the LPXTG motif, + represent positively charged residues and R is the repeat region. In ClfA Region A comprises N123 (not shown). The BCD region of FnBPA (and the shorter CD region of FnBPB—not shown) binds fibronectin.

Figure 12:
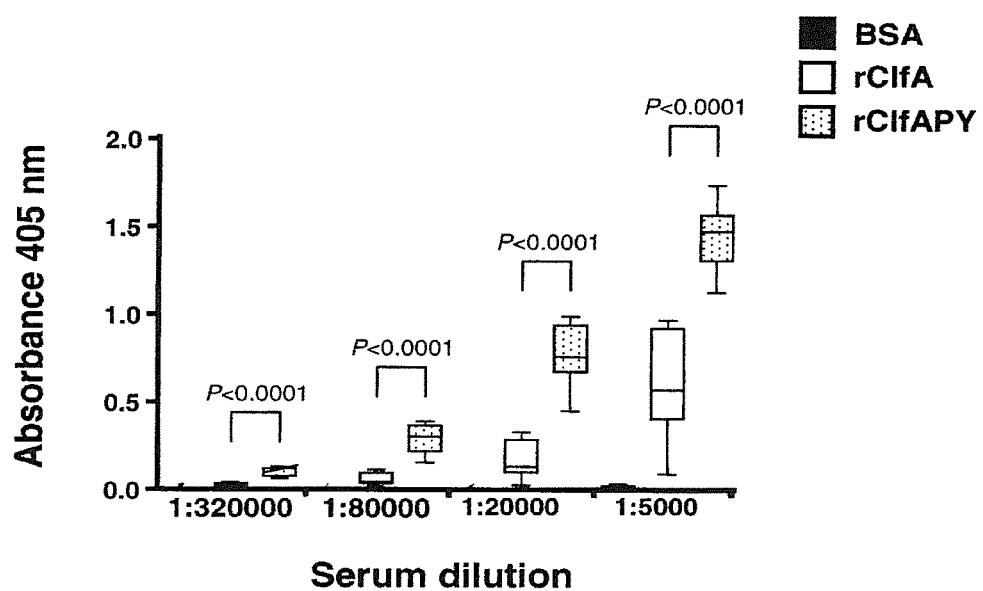

FIG. 12 shows the specific antibody responses to recombinant ClfAPY40-559 in serum samples of mice immunized with bovine serum albumin (BSA), recombinant ClfA40-559 (rClfA), or recombinant ClfAPY40-559 (rClfAPY), 9 days after the second booster immunization, which was one day before infection with $2.3 \times 10^7$ cfu/mouse of S. aureus strain Newman wildtype for induction of sepsis. Data are presented as medians (center lines), interquartile ranges (boxes), and 80% central ranges (whiskers). $N_{BSA}$=13-15, $N_{rClfA}$=15, and $N_{rClfAPY}$=15.

Figure 13:
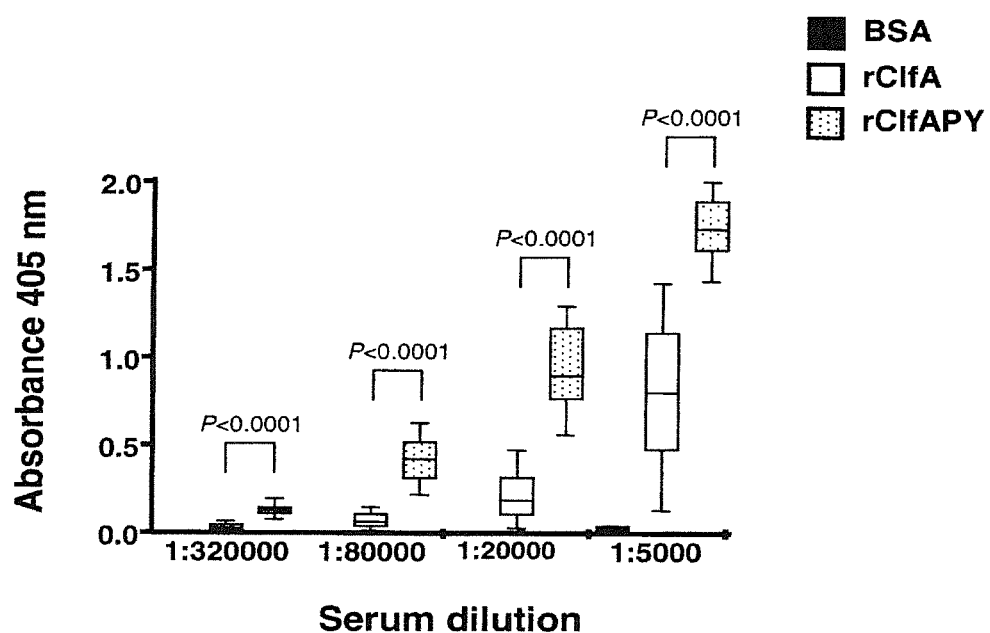

FIG. 13 shows the specific antibody responses to recombinant ClfA40-559 in serum samples of mice immunized with bovine serum albumin (BSA), recombinant ClfA40-559 (rClfA), or recombinant ClfAPY40-559 (rClfAPY), 9 days after the second booster immunization, which was one day before infection with $2.3 \times 10^7$ cfu/mouse of S. aureus strain Newman wildtype for induction of sepsis. Data are presented as medians (center lines), interquartile ranges (boxes), and 80% central ranges (whiskers). $N_{BSA}$=13-15, $N_{rClfA}$=15, and $N_{rClfAPY}$=15.

Figure 14:
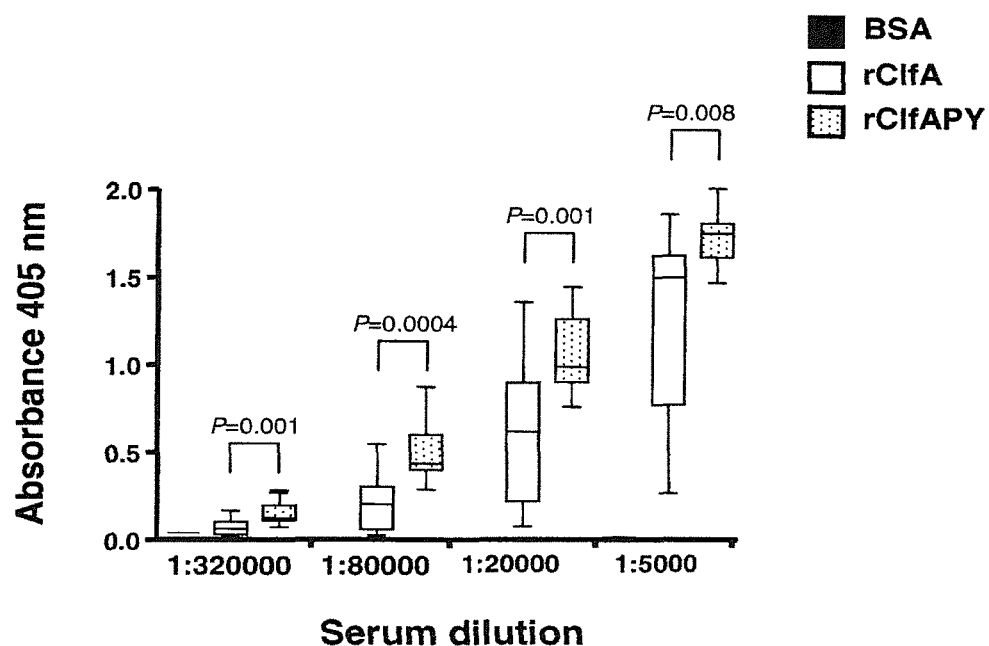

FIG. 14 shows the specific antibody responses to recombinant ClfAPY40-559 in serum samples of mice immunized with bovine serum albumin (BSA), recombinant ClfA40-559 (rClfA), or recombinant ClfAPY40-559 (rClfAPY), 9 days after the second booster immunization, which was one day before infection with $4.0 \times 10^6$ cfu/mouse of S. aureus strain Newman wildtype for induction of septic arthritis. Data are presented as medians (center lines), interquartile ranges (boxes), and 80% central ranges (whiskers). $N_{BSA}$=14-15, $N_{rClfA}$=15, and $N_{rClfAPY}$=15.

Figure 15:
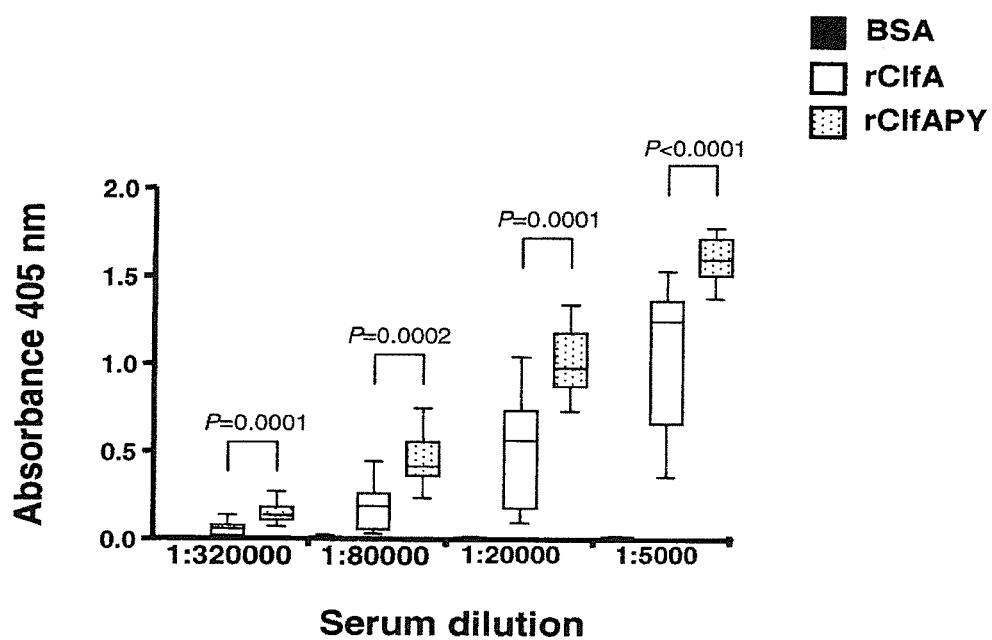

FIG. 15 shows the specific antibody responses to recombinant ClfA40-559 in serum samples of mice immunized with bovine serum albumin (BSA), recombinant ClfA40-559 (rClfA), or recombinant ClfAPY40-559 (rClfAPY), 9 days after the second booster immunization, which was one day before infection with $4.0 \times 10^6$ cfu/mouse of S. aureus strain Newman wildtype for induction of septic arthritis. Data are presented as medians (center lines), interquartile ranges (boxes), and 80% central ranges (whiskers). $N_{BSA}$=14-15, $N_{rClfA}$=15, and $N_{rClfAPY}$=15.

Figure 16:
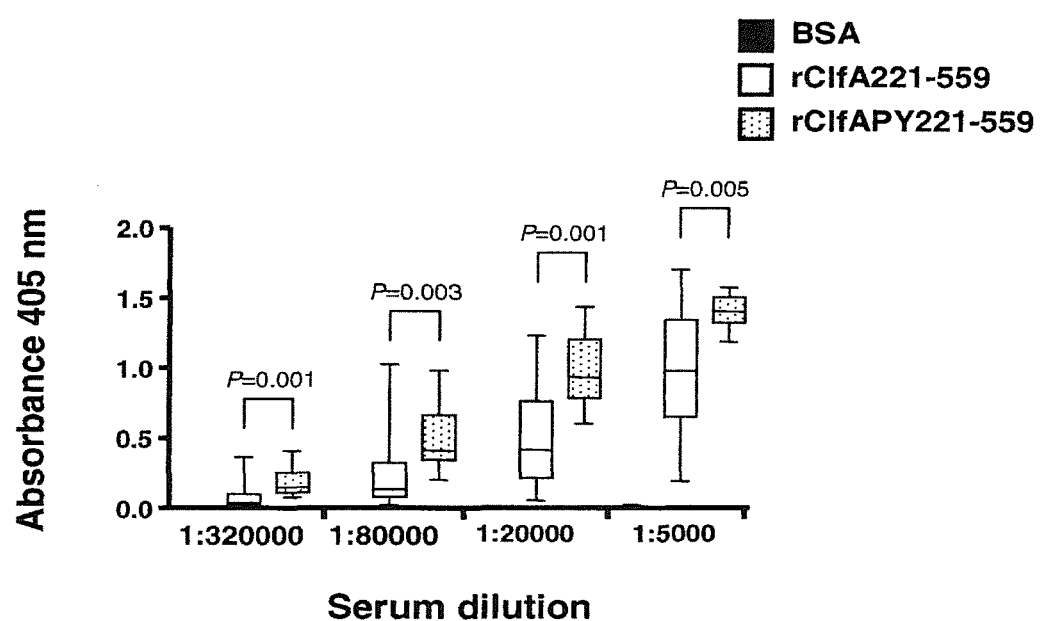

FIG. 16 of Example 2 shows the specific antibody responses to recombinant ClfAPY221-559 in serum samples of mice immunized with bovine serum albumin (BSA), recombinant ClfA221-559 (rClfA221-559), or recombinant ClfAPY221-559 (rClfAPY221-559), 9 days after the second booster immunization. Data are presented as medians (center lines), interquartile ranges (boxes), and 80% central ranges (whiskers). $N_{BSA}$=15, $N_{rClfA221-559}$=14-15, and $N_{rClfAPY221-559}$=14-15.

Figure 17:
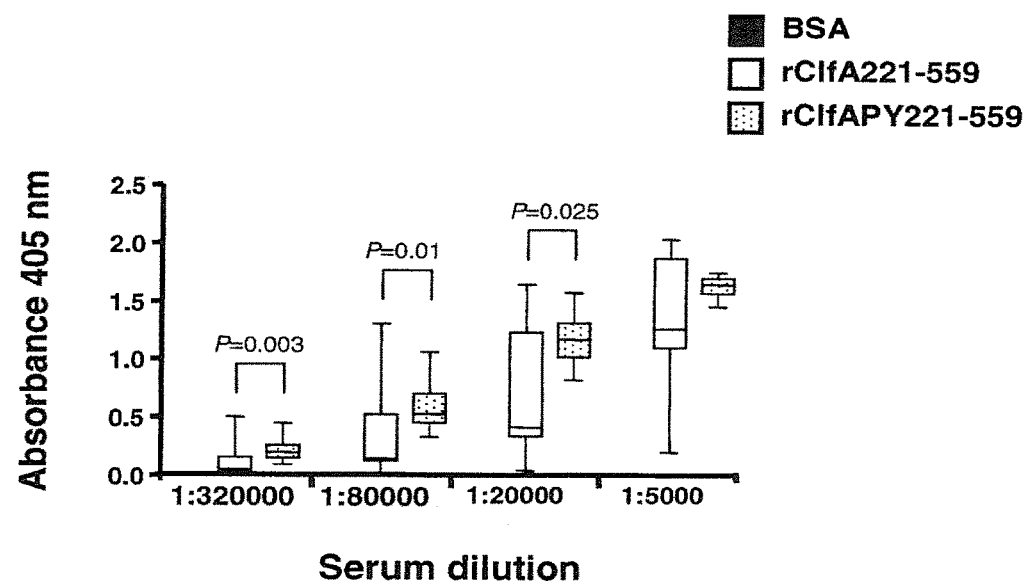

FIG. 17 of Example 2 shows the specific antibody responses to recombinant ClfA221-559 in serum samples of mice immunized with bovine serum albumin (BSA), recombinant ClfA221-559 (rClfA221-559), or recombinant ClfAPY221-559 (rClfAPY221-559), 9 days after the second booster immunization. Data are presented as medians (center lines), interquartile ranges (boxes), and 80% central ranges (whiskers). $N_{BSA}$=15, $N_{rClfA221-559}$=14-15, and $N_{rClfAPY221-559}$=14-15.

Figure 18:
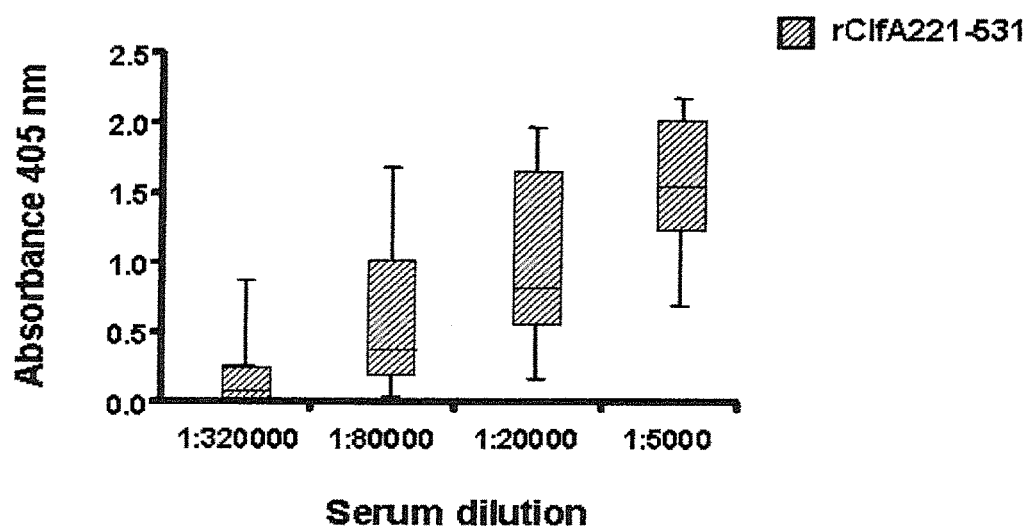

FIG. 18 of Example 3 shows the specific antibody responses to recombinant ClfA221-531 in serum samples of mice immunized with recombinant ClfAPY221-531 (rClfAPY221-531), 9 days after the second booster immunization. Data are presented as medians (center lines), interquartile ranges (boxes), and 80% central ranges (whiskers). $N_{rClfA221-531}$=14-15.

EXAMPLES

Example 1 rClfA A Region Truncates Comprising N1, N2 and N3 (Amino Acids 40-559)

Material and Methods

Full details of the numeric references in brackets given in the Examples are provided at the end of this section.

Mice

NMRI mice were obtained from Scanbur BK (Sollentuna, Sweden) and were maintained in the animal facility of the Department of Rheumatology, University of Göteborg, Sweden. Göteborg animal experiment ethical board approved the experiments. They were housed up to 10 animals per cage with a 12 h light-dark cycle, and were fed standard laboratory chow and water ad libitum. The animals were 6 to 16 weeks old at the start of the experiments.

Bacterial Strains

For infection of animals the S. aureus wildtype strains Newman (14) and LS-1 (11) and constructed derivatives thereof were used. The clfA $P_{336}SY_{338}A$ (clfAPYI) and clfA $P_{336}AY_{338}S$ (clfAPYII) derivatives were constructed in strain Newman and transduced to strain LS-1 (see below). The deletion mutants Newman clfA2::Tn917 mutant DU5876 (3) and LS-1 clfA2::Tn917 mutant (J. R. Fitzgerald et al., unpublished) were also used. Bacteria were grown on blood agar plates for 48 h, harvested, and kept frozen at −20° C. in PBS containing 5% (wt/vol) BSA (Sigma Chemicals) and 10% (vol/vol) dimethyl sulfoxide. Before injection into animals, the bacterial suspensions were thawed, washed in PBS, and adjusted to appropriate cell concentrations. The number of viable bacteria was measured in conjunction with each challenge by cultivation on blood agar plates and counting colonies.

Construction of clfAPYI and clfAPYII Mutations in S. aureus Newman and LS-1

In this experiment, a full length ClfA A region truncate, comprising N1, N2 and N3, corresponding to amino acids 40 to 559, was used. In the following description and figures:

ClfA may also be referred to as rClfA 40-559 (SEQ ID NO 3);

ClfA $P_{336}SY_{338}A$ may also be referred to as clfAPYI, rclfAPY or rclfAPYI (i.e clfAPYI 40-559) (SEQ ID NO 4); and ClfA $P_{336}AY_{338}S$ may also be referred to as clfAPYII, rclfAPYII (i.e. clfAPYII 40-559) (SEQ ID NO 5).

A 1.02 kb PstI-BamHI fragment of pCF77 PY (Loughman et al., 2005) containing the mutations $P_{336}S$ and $Y_{338}A$ in clfA was cloned into pBluescriptII SK– (Stratagene). This plasmid was linearised with HindIII and ligated to HindIII-cut pTSermC (J. Higgins, unpublished) to generate plasmid pARM, which is a temperature sensitive E. coli-S. aureus shuttle vector containing the $P_{336}S$ and $Y_{338}A$ substitutions.

In order to reduce the risk of unknowingly generating a functional or immunoreactive epitope by substituting $P_{336}$ and $Y_{338}$, we generated a second mutant, in which the order of the substitutions was reversed, yielding $P_{336}A$ and $Y_{338}S$.

To generate this a plasmid pJH2, analogous to pARM but containing the $P_{336}A$ and $Y_{338}S$ substitutions, was generated. Overlap primer PCR was used with the same flanking primers used to make pCF77 PY (6), and a different pair of overlapping mutagenic primers:

F3:
GCAACTTTGACCATGGCCGCTTCTATTGACCCTGAAAATG
and

R3:
CATTTTCAGGGTCAATAGAAGCGGCCATGGTCAAAGTTGC (mutations in bold and underlined) to generate pCF77 PYII. The 1.02 kb PstI-HindIII fragment of this plasmid was used as described above to generate pJH2, a temperature sensitive E. coli-S. aureus shuttle vector containing the $P_{336}A$ and $Y_{338}S$ substitutions.

Both pARM and pJH2 were transferred to RN4220 (15) by electroporation and subsequently transduced using phage 85 (16) to S. aureus Newman (14) and LS-1 (11). In these strains the plasmids were induced to insert into the chromosome and then excise, leaving the mutations in the chromosome of a proportion of transformants, generating Newman clfAPYI, Newman clfAPYII, LS-1 clfAPYI and LS-1 clfAPYII. Transformants were screened for loss of the plasmid and a loss of fibrinogen-binding activity. Integrity of the clfA gene was verified by Southern hybridisation using a clfA probe (data not shown). Expression of an immunoreactive protein (ClfAPY) was verified by Western immunoblotting using anti-ClfA region A polyclonal rabbit antiserum (data not shown). The mutations were verified by PCR across the KpnI-BamHI fragments from genomic DNA and commercial sequencing of the products. The about 700 bases of the clfA gene of strain LS-1 that were sequenced were identical to the corresponding bases in the Newman clfA gene of strain Newman.

Production of Recombinant ClfA and ClfAPY

His-tagged recombinant ClfA region A, domains N123 (amino acids 40-559), was produced from pCF40 as previously described (17), with an additional polishing step through an anion-exchange column. Plasmid pCF77 PY (6) was used as template to clone clfAPYI domains N123 into pQE30 to generate pCF40PY. Using this plasmid, recombinant ClfAPY was also produced by nickel affinity chromatography and anion exchange chromatography, as was described for rClfA. Eluates were dialysed against two changes of PBS before concentration and freeze-drying.

Septic Arthritis and Sepsis Experiments

In experiments 1-3 all the mice (n=10 per group) were infected with strain Newman to trigger arthritis. In experiments 4 and 5, the mice were infected with strain Newman and LS-1, respectively, to induce sepsis (n=10 per group).

Experiment 1 Mice were infected by intravenous injection with $3.5 \times 10^6$ cfu/mouse of S.aureus strain Newman or with $4.3 \times 10^6$ cfu/mouse of Newman clfAPYI mutant, both in 200 μl PBS. Clinical arthritis and weight change was followed until day 7. Mice were sacrificed day 8, kidney growth of bacteria were assessed and serum IL-6 and total IgG levels were measured. Synovitis and bone destruction was studied histologically on the joints of fore and hind legs.

Experiment 2 Mice were infected with $5.0 \times 10^6$ cfu, $6.0 \times 10^6$ cfu or $4.3 \times 10^6$ cfu of S.aureus strain Newman, clfAPYI mutant or Newman clfA::Erm$^R$ (clfA null mutant), respectively. Clinical arthritis and weight change was followed until day 7. Mice were sacrificed day 7, kidney growth of bacteria were assessed and serum IL-6 and total IgG levels were measured. Synovitis and bone destruction was studied histologically on the joints of fore and hind legs.

Experiment 3 Mice were infected with $4.7×10^6$ cfu, $3.2×10^6$ cfu, $3.9×10^6$ cfu or $4.8×10^6$ cfu of S.aureus strain Newman, clfAPYI mutant, Newman clfAPYII mutant or Newman clfA null mutant, respectively. Clinical arthritis and weight change was followed until day 7. Mice were sacrificed day 8 and kidney growth of bacteria were assessed.

The outcome of the experiments 1-3 were very similar, so data were pooled and presented together.

In Experiment 4 mice were injected intravenously with $5.2×10^7$ cfu, $5.1×10^7$ cfu or $3.3×10^7$ cfu of S.aureus strain Newman, clfAPYI mutant or clfA null mutant, respectively. Mortality, weight change and clinical arthritis were followed until day 10.

In Experiment 5 mice were infected with $9.4×10^6$ cfu, $7.9×10^6$ cfu, $10.7×10^6$ cfu or $9.8×10^6$ cfu of S.aureus strain LS-1, LS-1 clfAPYI mutant, LS-1 clfAPYII mutant, or LS-1 clfA null mutant, respectively. Mortality, clinical arthritis and weight change was followed until day 16.

Infra-Articular Injection of Bacteria

One knee joint per mouse was injected with $2.4×10^4$ cfu, $2.4×10^4$ cfu, or $3.4×10^4$ cfu of strain Newman wildtype, clfAPYI mutant or clfA knockout mutant, respectively, in 20 µl PBS. N=10 per group. Mice were sacrificed 3 days later, and the knee joints were collected for histopathological examination.

Vaccination with Wild-Type and Mutant Recombinant ClfA

Purified rClfA40-559, rClfAPY40-559 (i.e. rClfAPYI) or BSA were dissolved in physiologic saline and emulsified 1:1 in Freund's complete adjuvant (Difco Laboratories). Two hundred µl of the emulsion containing 30 µg (=0.53 nmol) of protein was injected subcutaneously (s.c.) on day 0. First booster immunization with 30 µg of protein in physiologic saline in incomplete Freund's adjuvant was performed on day 11. Second booster immunization was done day 21. On day 30 the mice were bled and sera were frozen for later analysis of antibody responses.

On day 31, 14-15 mice per group were infected by i.v. injection of $4.0×10^6$ cfu/mouse for induction of septic arthritis, or by $2.3×10^7$ cfu/mouse for induction of sepsis. Clinical arthritis, weight change and mortality were followed for 11 and 15 days, respectively. Bacterial growth in kidneys was assessed in the septic arthritis experiment.

Clinical Evaluation of Infected Mice

The clinical evaluation was performed in a blinded manner. Each limb was inspected visually. The inspection yielded a score of 0 to 3 (0, no swelling and erythema; 1, mild swelling and/or erythema; 2, moderate swelling and/or erythema; 3 marked swelling and/or erythema). The arthritic index was constructed by adding the scores from all four limbs of an animal. The overall condition of each mouse was also examined by assessing signs of systemic inflammation, i.e., weight decrease, reduced alertness, and ruffled coat. In cases of severe systemic infection, when a mouse was judged too ill to survive another 24 h, it was killed by cervical dislocation and considered dead due to sepsis.

Histological Examination

Histological examination of joints was performed using a modification (8) of a previously described method (18).

Bacteriologic Examination of Infected Kidneys

Kidneys were aseptically dissected, kept on ice, homogenised, serially diluted in PBS and spread on blood agar plates. After 24 h of incubation in 37° C. the number of cfu per kidney pair was determined.

Measurement of Serum IgG

Levels in serum of total IgG were measured by the radial immunodiffusion technique (19). Goat-Anti-Mouse-IgG and mouse IgG standard were purchased from Southern Biotech, Birmingham, Ala.

Specific Antibodies—ELISA

Serum samples from immunized mice were obtained 9 days after the second booster immunization. The serum specific antibody response against rClfA and rClfAPY was measured by ELISA. Microplates (96-well; Nunc) were coated with 5 µg/ml of recombinant protein in PBS. Blocking agent, serum samples, biotinylated antibodies, and ExtrAvidin-proxidase were all diluted in PBS. The assay was run according to a previous description (8). All serum samples were diluted 1:20000, and antibody response was monitored as absorbance at 405 nm.

In a second run, to get a more accurate measure of the specific antibody responses in the different immunization groups, the responses were determined at several serum dilutions. Thus, all serum samples were diluted 1:5000, 1:20000, 1:80000 and 1:320000, and antibody response was monitored as absorbance at 405 nm.

IL-6 Analysis

Serum IL-6 was detected by a method previously described (20).

Statistical Analysis

Statistical evaluation was done by using the Mann-Whitney U test. P<0.05 was considered to be significant. Data are reported as medians, interquartile ranges, and 80% central ranges, unless otherwise mentioned.

Results

Figure 1:
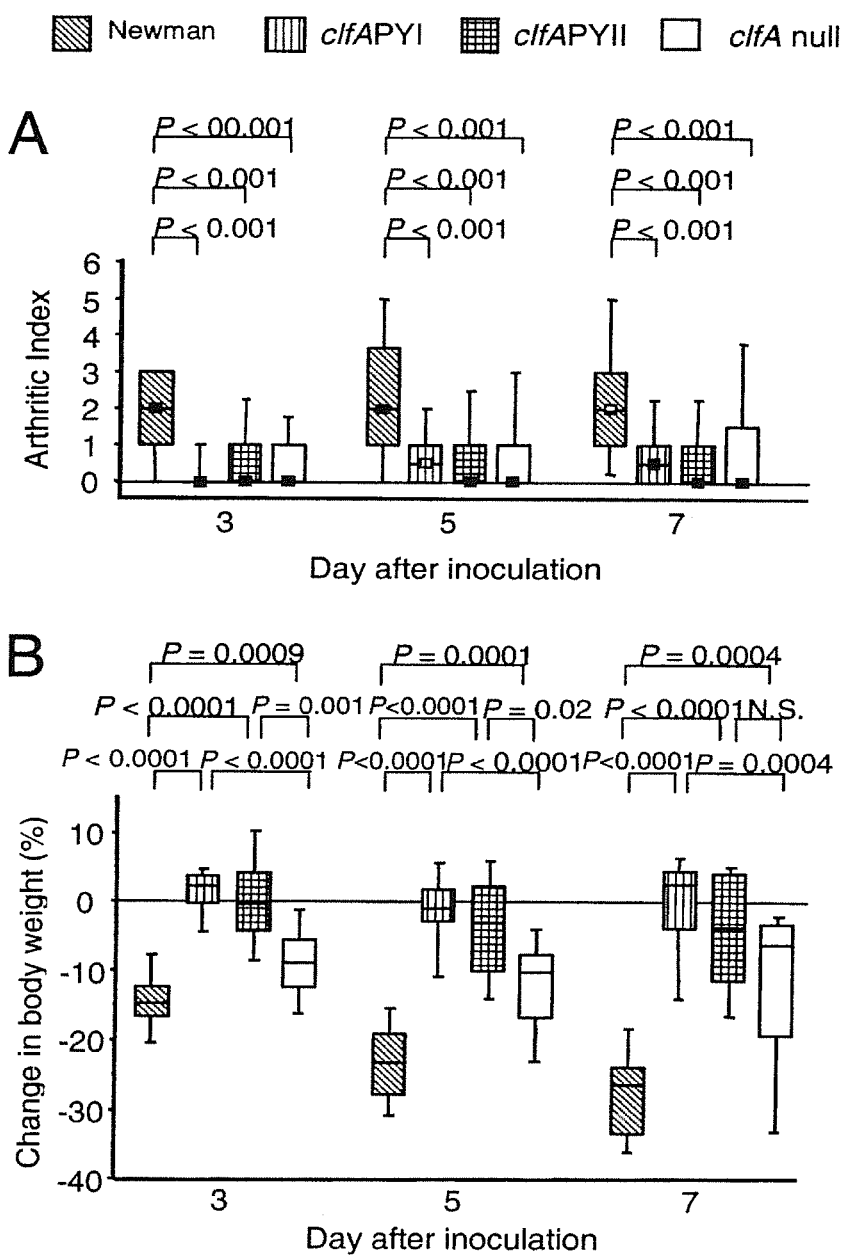

Exchange of Two Amino Acids Necessary for ClfA Binding to Fibrinogen Hampers Development of Septic Arthritis and Sepsis Two amino acids (P336 and Y338) that are known to be required for fibrinogen binding by ClfA were altered by allelic exchange to create mutants of strains Newman and LS1 that expressed a non-fibrinogen-binding ClfA protein on the cell surface. The level of expression and integrity of the protein was measured by Western blotting which established that there was good expression of the mutant proteins on the bacterial surface and expressed protein was the right size.

The ability of Newman wild-type and Newman clfA $P_{336}S$ $Y_{338}A$ (clfAPYI) to provoke septic arthritis was investigated. Septic arthritis was induced by intravenous inoculation of $3.5\times10^6$ to $5.0\times10^6$ colony-forming units (cfu) and $3.2\times10^6$ to $6.0\times10^6$ cfu of Newman wild-type and the clfAPYI mutant, respectively. The development of arthritis was studied clinically for 7 days. The clfAPYI mutant provoked significantly less severe arthritis than the wild-type strain over the entire experimental period ($P>0.001$, FIG. 1 A). The frequency of arthritis was lower for Newman clfAPYI at most time points (FIG. 6).

Unexpectedly, it appears that the new amino acid composition in the ClfAPYI molecule fits for interaction with a host anti-bacterial defense. To check for this possibility, a new construct was made where different amino acids were substituted for P336 and Y338 (clfA $P_{336}A$ $Y_{338}S$: clfAPYII). Mice that were inoculated with $3.9\times10^6$ cfu of Newman clfAPYII developed arthritis to the same low extent as the clfAPYI mutant (FIG. 1 A), and with a similar frequency (FIG. 6). This outcome suggests strongly that the loss of fibrinogen binding is responsible for the reduced level of arthritis.

It is possible that ClfA is involved in the development of arthritis by mechanisms that do not involve fibrinogen binding. To test this a ClfA deletion mutant lacking the ClfA protein was compared to mutants expressing the modified non-fibrinogen binding ClfA protein. However, mice that were infected with $4.3 \times 10^6$ to $4.8 \times 10^6$ cfu of clfA null mutant developed arthritis in a manner not different from the clfAPYI and clfAPYII mutant infected mice (FIG. 1 A). The frequency of arthritis was also indistinguishable (FIG. 6).

Infected joints were also investigated histologically. The synovitis in Newman clfAPYI-infected mice was significantly milder than in wild-type infected mice in both experiment 1 and 2 (P=0.02 and 0.001, respectively). Bone destruction, a major cause of sequels in human septic arthritis, was almost absent in the Newman clfAPYI-infected samples (Experiment 2, P=0.001). The synovitis and bone destruction induced by the Newman clfA null mutant were also less pronounced compared to mice infected with Newman wild-type (P=0.003 and 0.006, respectively), but somewhat more severe than in the Newman clfAPYI group, although not significantly so.

Next, the metabolic consequences of the clfA mutations for the infectious process were analysed. Mice infected with the Newman wild-type strain lost up to about 30% of their body weight during the experimental period. Mice that were infected with the fibrinogen binding-deficient mutants Newman clfAPYI and Newman clfAPYII lost hardly any weight at all (P>0.0001 versus wild-type). In contrast, the Newman clfA null mutant had an intermediate effect on the weight loss, causing significantly less than the wild-type strain, but significantly more than the clfAPYI and clfAPYII mutant strains (P≤0.02 in most cases, FIG. 1 B).

The serum levels of IL-6, a measure of systemic inflammatory response, were analyzed at day 7-8 of infection. The pattern of IL-6 expression was similar to weight changes. Newman wild-type evoked high levels of serum IL-6 (4.8 (2.8, 5.7) ng/ml), the Newman clfAPYI mutant evoked considerably lower IL-6 (0.2 (0.07, 2.4) ng/ml, P<0.0001) while the Newman clfA null mutant gave rise to an intermediate response (2.5 (1.3, 3.2) ng/ml) with significant differences to both the wild-type and clfAPYI mutant group (P=0.009 and P=0.008, respectively) (median, interquartile range).

Figure 2:
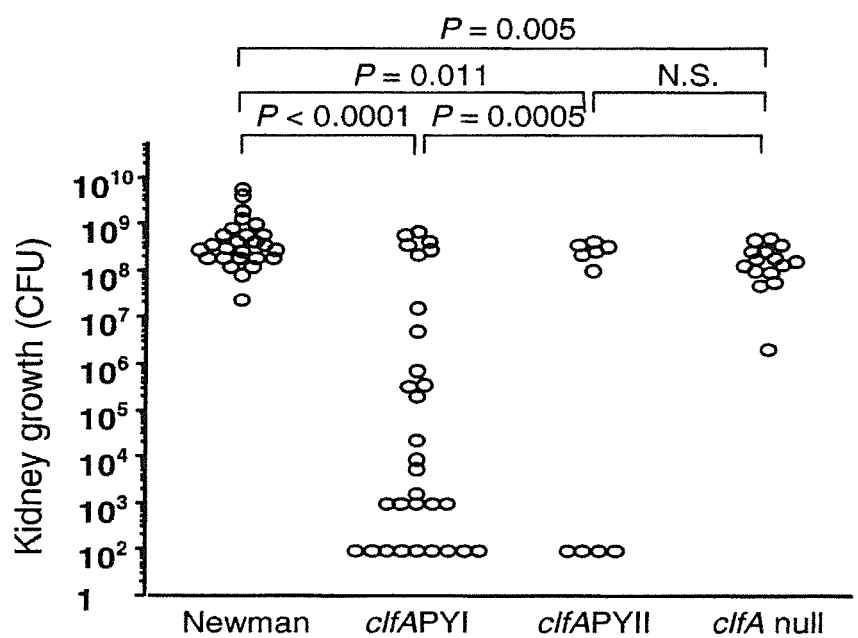

The growth of bacteria in kidneys was significantly greater in Newman wild-type-infected mice, compared to both of the Newman clfAPY mutants and the Newman clfA null mutant (P<0.0001, P=0.011, and P=0.005, respectively; FIG. 2). The Newman clfA null mutant-infected mice had significantly more bacterial growth in kidneys than Newman clfAPYI-infected mice (P=0.0005, FIG. 2).

Total IgG in sera was measured in mice on day 7-8 of infection. There was a significantly lower increase of IgG levels in both the Newman clfAPYI- and Newman clfA null mutant-infected groups as compared to mice infected with the wild-type strain (3.1 (1.2, 4.9); 2.3 (1.0, 2.6); and 6.4 (5.0, 11.0), respectively (median, interquartile range); P≤0.0003). There were no significant differences between the two mutant groups.

The mortality was 17% in the Newman wild type-infected mice, 0% in the Newman clfAPYI and clfAPYII mutant groups and 30% in the Newman clfA null mutant group. There were significant differences in mortality between the wild-type and the clfAPYI groups, and between the clfAPYI and clfA null mutant groups (P<0.05 and P<0.01, respectively).

It appears that direct and indirect signs of systemic inflammation are lower in mice infected with *S. aureus* expressing ClfA that is deficient in fibrinogen binding. Unexpectedly, the strain which lacked ClfA expression altogether induced more systemic inflammation than a ClfAPY mutant-expressing strain.

Figure 3:
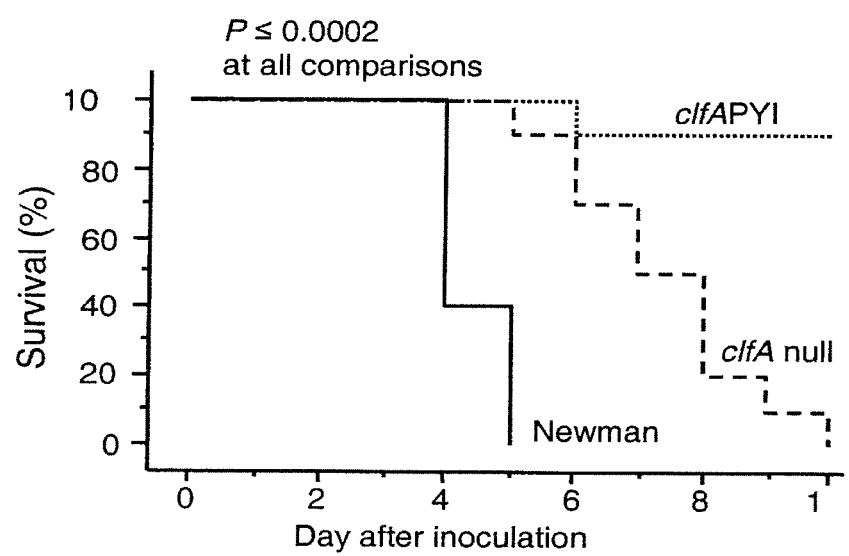
FIG. 3 shows the survival of mice after inoculation with 5.2, 5.1 or $3.3 \times 10^7$ cfu of S.aureus strain Newman, clfAPYI mutant or clfA null mutant, respectively. N=10 per group from start.

Sepsis was induced in mice by increasing the inoculation dose of *S. aureus*. Mice were infected with $5.2 \times 10^7$ cfu of Newman wild type, $5.1 \times 10^7$ cfu of the Newman clfAPYI mutant and $3.3 \times 10^7$ cfu of the Newman clfA null mutant. Within 5 days all wild-type infected mice were dead, but only one clfAPYI mutant mouse out of ten were dead after 10 days of infection (P<0.0001, FIG. 3). Mice infected with the clfA null mutant also survived a significantly shorter time than the clfAPYI mutant-infected mice (P<0.0001, FIG. 3). In this experiment the mice challenged with the clfA null mutant developed significantly more arthritis than the clfAPYI mutant group, while at the same time they lost significantly more weight (FIGS. 7 and 8). Thus, by analogy with the measures of systemic inflammation in the septic arthritis experiments, the survival of the mice is prolonged if the ClfA molecule is expressed, as long as it lacks fibrinogen binding properties.

Injection of Bacteria into Joints

To test if the inflammatory reaction in the joint is dependent on fibrinogen binding, Newman wild-type, Newman clfAPYI or Newman clfA null were injected directly into a knee joint of mice, thereby by-passing the systemic compartment. Synovitis, including polymorphonuclear infiltration of the joint cavity, and bone destruction was studied by histology 3 days later. The mice received $2.4 \times 10^4$ cfu of wild-type, $2.4 \times 10^4$ cfu of the clfA null mutant, or $3.4 \times 10^4$ cfu of clfAPYI mutant in one knee. The synovitis and the polymorphonuclear infiltration histologic index in the joint cavity was 0.25 (0, 3.0) for knees infected with wild-type, 2.38 (0.25, 3.0) for the clfA null mutant and 0.25 (0, 0.25) for the clfAPYI mutant (median, interquartile range). The histologic index for destruction of bone was 0 (0, 1.0) for wild-type, 1.0 (0, 1.0) for the clfA null mutant, and 0 (0, 0) for the clfAPYI mutant (median, interquartile range; P=0.01 between the clfAPYI mutant and the clfA null mutant). Since the clfA FYI mutant evoked very little synovitis and destruction, despite the fact that 42% more of that strain was given to mice than the other strains, it is concluded that ClfA-promoted fibrinogen binding is needed for the maximal inflammatory response within the joint. Again, the absence of ClfA expression enhanced inflammation compared to the fibrinogen binding deficient ClfA mutant.

PY Mutation in Strain LS-1

Figure 4:
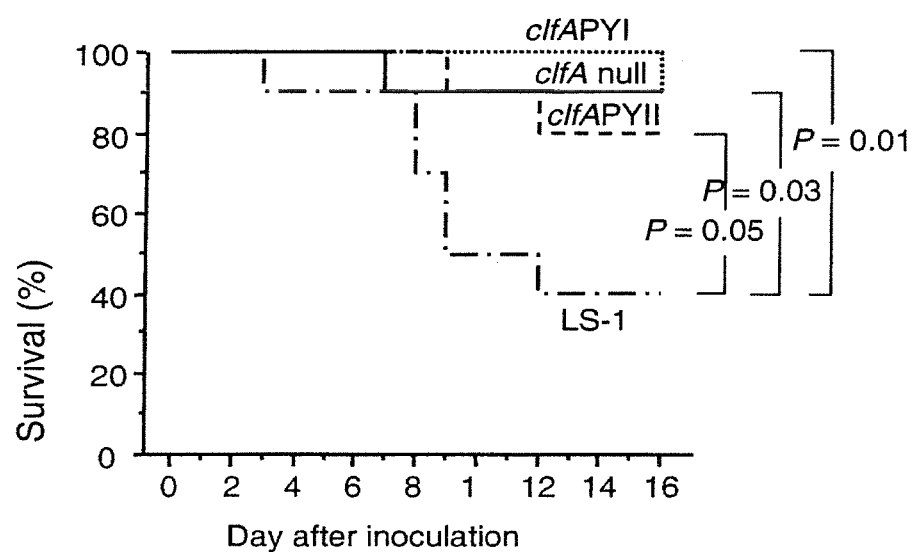
FIG. 4 shows the survival of mice after inoculation with 9.4, 7.9, 10.7 or $9.8 \times 10^6$ cfu of S.aureus strain LS-1, and clfAPYI, clfAPYII or clfA null mutants, respectively. N=15 per group from start.

To determine if the ability of ClfA to bind fibrinogen affects virulence of other strains of *S. aureus*, the clfAPYI, clfAPYII and clfA null mutations were transduced to the TSST-1 expressing *S. aureus* strain LS-1. Mice were challenged with $9.4 \times 10^6$ cfu of LS-1 wild-type, $7.9 \times 10^6$ cfu of LS-1 clfAPYI, $10.7 \times 10^6$ cfu of LS-1 clfAPYII, or $9.4 \times 10^6$ cfu of the LS-1 clfA null mutant. Sepsis was studied by following the survival rate. After 16 days only 40% of mice challenged with the wild-type strain were alive while 90% of the mice challenged with the clfAPYI mutant and clfA null mutant groups and 80% mice infected with the clfAPYII mutant were alive (FIG. 4). The clfAPYI mutants and the clfA null mutant of LS-1 were significantly less virulent (P=0.014, P=0.05 and P=0.03, respectively).

Immunization with Recombinant ClfA Proteins

The effect of vaccination with recombinant wild-type ClfA A domain protein (rClfA) and mutant ClfAPYI protein (rClfAPY) was studied in both the septic arthritis model and the sepsis model. Mice were sensitized and then boosted twice with control protein BSA, rClfA, or rClfAPY, and subsequently infected with $4.0 \times 10^6$ cfu of *S. aureus* strain Newman to induce septic arthritis, or with $2.3 \times 10^7$ cfu of strain Newman to induce sepsis. Immunization with rClfAPY (i.e. ClfAPYI recombinant protein A domain) protected significantly against septic death as compared to control mice (P=0.01, FIG. 5) while rClfA immunization did not achieve significant protection. One day before bacterial infection there was a much higher specific serum antibody response to both rClfAPY and rClfA in mice immunized with rClfAPY ($A_{405}$=0.39 (0.33, 0.56) and 0.71 (0.52, 0.81)) as compared to mice immunized with rClfA ($A_{405}$=0.13 (0.07, 0.17) and 0.15 (0.10, 0.24), P<0.0001 in both comparisons (median, interquartile range)). Control immunized animals had only background levels ($A_{405\ nm}$=0 and 0.01 (0, 0.01) (median, interquartile range)). The immunized mice which were to be infected with the lower, arthritic bacterial dose had similar antibody responses to rClfA and rClfAPY as the mice in which sepsis were induced (data not shown). Immunization with both rClfA and rClfAPY protected against the development of arthritis, although the protection was not significant (FIG. 9).

During day 5 to 9 after infection the weight loss was significantly reduced in the rClfAPY and rClfA immunized mice, as compared to the control mice (data not shown).

A trend to diminished bacterial growth in kidneys of mice immunized with rClfAPY or rClfA at day 11 after infection (BSA: 38 (3, 436); rClfAPY: 7 (2, 17); rClfA: 10 (7, 54)×$10^7$ cfu/kidney pair) was observed.

To get a more accurate measure of the specific antibody responses in the different immunization groups, the responses were determined at several serum dilutions (the second run). Data shows that there were very likely higher titers of specific antibodies in sera from rClfAPY immunized mice to both the rClfAPY and rClfA wildtype antigens, in both the mice which were to be infected with the septic and the arthritic bacterial dose, respectively, than in sera from rClfA wildtype immunized mice, since there was significantly higher antibody responses measured as absorbance in mice immunized with rClfAPY at each serum dilution in all comparisons (P<0.0001 to P=0.008, FIG. 12-15). BSA immunization evoked only a background antibody response.

Conclusion

The results strongly suggest that the ClfA-fibrinogen interaction is crucial for the bacterial virulence and disease outcome. The ability of ClfA to bind fibrinogen was associated with enhanced virulence in terms of the ability to cause septic death. In both staphylococcal strains tested, a clfAPY mutant induced less septic death than the wild-type. Also, the severity of arthritis was strongly reduced in mice infected with the non-fibrinogen binding clfAPY mutant.

A likely mechanism for the promotion of virulence by the fibrinogen-bacterial cell surface interaction is inhibition of neutrophil phagocytosis (5). Neutrophils are crucial for the host defense in the early phase of S. aureus infection (13). Without neutrophils, bacterial growth is strongly augmented in blood and kidneys, and the frequency of arthritis and mortality increases. Fibrinogen mediated inhibition of neutrophil phagocytosis by ClfA could explain at least in part the more pronounced virulence of wildtype S. aureus compared to the clfAPY mutants. Binding of fibrinogen to ClfA could decrease opsonophagocytosis by neutrophils by reducing opsonin deposition or access to opsonins by neutrophil receptors. Alternatively bound fibrinogen might block the binding of an unknown protective host factor to S. aureus. Another option is that the fibrinogen-ClfA interaction promotes bacterial passage from blood vessel into the tissue or promotes colonization in tissues.

Unexpectedly, our data also show the ClfA null mutant was more virulent than the clfAPY mutant strains. Possibly the ClfA protein has functions in vivo other than interacting with fibrinogen. This interaction is clearly disadvantageous for the host as shown in this study. Other functions of ClfA are presently not well mapped but non-fibrinogen dependent platelet aggregation exerted by ClfA might result in trapping of big amounts of S. aureus in circulation with subsequent elimination of the bacterial-platelet complexes through the reticuloendothelial system. Such platelet aggregation mediated elimination of staphylococci would readily occur in the wild-type and clfAPY mutated strains but not in the clfA knockout. Whereas in the wild-type strain the fibrinogen interaction would overshadow the other events, in the clfAPY mutants such bacterial elimination might be highly beneficial to the host.

The clfA knockout mutant protected against septic death to the same degree as the clfAPY mutation in S. aureus strain LS-1, but protected less, if at all, in strain Newman. The overall impact of ClfA expression on bacterial virulence could differ between different S. aureus strains depending on the level of expression and the presence of other virulence factors.

The issue whether the clfAPY mutant displays equal or lower virulence once in the joint cavity is of certain importance having in mind that in inflamed synovial fluid fibrinogen and fibrin are abundant. Our data suggest that the clfAPY mutant is less destructive for cartilage and bone.

The protective effect of recombinant ClfA A domain non-fibrinogen binding $P_{336}Y_{338}$ mutant was greater than for wildtype rClfA. Immunization with ClfAPY very likely induced a better immune response since higher specific antibody responses were evoked against both the immunogen and the wildtype ClfA protein. More importantly, it induced a greater protective immune response against septic death than wildtype ClfA.

In conclusion, our results show that rClfAPY is a better vaccine candidate than wild type recombinant ClfA. We hypothesize that binding of fibrinogen by wild-type ClfA protein during the immunization phase decreases antigen presentation due to hiding of important epitopes on the ClfA molecule and hence impairs specific antibody production.

Example 2 rClfA A Region Truncate Comprising N2 and N3 (rClfA 221-559)

Materials & Methods:

The protocols outlined in Example 1 were followed in this example which utilized
rClfA 221-559 (i.e. ClfA A region truncate comprising N2 and N3 corresponding to amino acids 220-559)
rClfAPY221-559; and
BSA.

There were 15 female NMRI mice per group who were 8 weeks old at start of experiments. In this Example, the constructs used for immunization were ClfA wild type/native N2N3 truncate, ClfA N2N3 truncate with mutation PY as defined in Example 1. BSA was used as the control.

Vaccination with Wild-Type and Mutant Recombinant ClfA

The mice were immunized with rClfA 221-559, rClfAPY 221-559 or BSA in accordance with the protocol of Example 1.

Purified rClfA221-559, rClfAPY221-559 (i.e. ClfAPYI recombinant protein A subdomains N2 and N3) or BSA were dissolved in PBS and emulsified 1:1 in Freund's complete adjuvant. Two hundred μl of the emulsion containing 30 μg (=0.79 nmol) of protein was injected s.c. on day 0.

First booster immunization with 30 µg of protein in physiologic saline in incomplete Freund's adjuvant was performed on day 12. Second booster immunization was done day 22. On day 31 the mice were bled and sera were frozen for later analysis of antibody responses.

Specific Antibodies—ELISA

Serum samples from immunized mice were obtained 9 days after the second booster immunization. The serum specific antibody response against rClfA221-559 and rClfAPY221-559 was measured by ELISA. Microplates (96-well; Nunc) were coated with 5 µg/ml of recombinant protein in PBS. Blocking agent, serum samples, biotinylated antibodies, and ExtrAvidin-proxidase were all diluted in PBS. The assay was run according to a previous description (8). All serum samples were diluted 1:5000, 1:20000, 1:80000 and 1:320000, and antibody response was monitored as absorbance at 405 nm.

Results:

Specific Antibody Response:

The antibody response was measured by absorbance in an ELISA-assay, as per Example 1, with four different serum dilutions. The data obtained was very similar to the data in the Example 1.

It was found that rClfAPY221-559 immunization very likely gave rise to higher titers of specific antibodies to both native rClfA221-559 and rClfAPY221-559, as compared to native rClfA221-599 immunization, since there were significantly higher antibody responses measured as absorbance in mice immunized with rClfAPY221-559 at each serum dilution in all comparisons but one (P=0.001 to 0.025, see FIGS. 16 and 17). BSA immunization evoked only background levels of antibody response.

Conclusion

We found that immunization with a rClfAPY221-559 protein gave rise to significantly higher antibody responses to both the immunogen and the wildtype ClfA protein, than immunization with the native protein.

Based on these findings, we conclude that PY-immunization, regardless if the PY protein comprises amino acids 40 to 550 as in Example 1 or amino acids 221 to 559 as in Example 2, induces a better immune response than immunization with native ClfA of the corresponding size.

Example 3

ClfA A Region Truncate (δ/Delta Latch Truncate)

Materials & Methods:

The protocols outlined in Example 1 were followed in this example which utilized the following construct:

rClfA 221-531 (i.e. rClfA A region truncate comprising N2 and N3 amino acids 220-559 but without the latching peptide amino acids 532-538 and the subsequent proline-rich residues.

There were 15 female NMRI mice in the group who were 8 weeks old at start of experiment. In this Example, the above construct was used for immunization. The mice were immunized with the above truncate in accordance with the protocol of Example 1.

Vaccination with Wild-Type and Mutant Recombinant ClfA

Purified rClfA221-531 was dissolved in PBS and emulsified 1:1 in Freund's complete adjuvant. Two hundred µl of the emulsion containing 0.79 nmol of protein was injected s.c. on day 0. First booster immunization with 0.79 nmol of protein in physiologic saline in incomplete Freund's adjuvant was performed on day 12. Second booster immunization was done day 22. On day 31 the mice were bled and sera were frozen for later analysis of antibody responses.

Specific Antibodies—ELISA

Serum samples from immunized mice were obtained 9 days after the second booster immunization. The serum levels of specific antibodies was measured by ELISA. Microplates (96-well; Nunc) were coated with 4.6 µg/ml of rClfA221-531 protein which is equimolar to 5 µg/ml of rClfA221-559 and rClfAPY221-559 from Examples 1 and 2. Blocking agent, serum samples, biotinylated antibodies, and ExtrAvidin-proxidase were all diluted in PBS. The assay was run according to a previous description (8). All serum samples were diluted 1:5000, 1:20000, 1:80000 and 1:320000, and antibody response was monitored as absorbance at 405 nm.

Results:

The antibody response was measured by absorbance in an ELISA-assay, as per Example 1. It was found that rClfA221-531 immunization gave rise to an immune response, measured as a specific antibody response (FIG. 18).

Conclusion

We found that rClfA221-531 works as an immunogen, since the antigen evokes a specific antibody response.

REFERENCES

1. Peacock S J, Moore C E, Justice A, Kantzanou M, Story L, Mackie K, O'Neill G, Day N P J (2002) Virulent combinations of adhesin and toxin genes in natural populations of *Staphylococcus aureus*. *Infect Immun* 70:4987-4996.
2. McDevitt D, Nanavaty T, House-Pompeo K, Bell E, Turner N, McEntire L, Foster T, Höök M (1997) Characterization of the interaction between the *Staphylococcus aureus* clumping factor (ClfA) and fibrinogen. *Eur J Biochem* 247:416-424.
3. McDevitt D, Francois P, Vaudaux P, Foster T J (1994) Molecular characterization of the clumping factor (fibrinogen receptor) of *Staphylococcus aureus*. *Mol Microbiol* 11:237-248.
4. Palmqvist N, Patti J M, Tarkowski A, Josefsson E (2004) Expression of staphylococcal clumping factor A impedes macrophage phagocytosis. *Microb Infect* 6:188-195.
5. Higgins J, Loughman A, van Kessel K P M, van Strijp J A G, Foster T J (2006) Clumping factor A of *Staphylococcus aureus* inhibits phagocytosis by human polymorphonuclear leukocytes. *FEMS Microbiol Lett* 258:290-296.
6. Loughman A, Fitzgerald J R, Brennan M P, Higgins J, Downer R, Cox D, Foster T J (2005) Roles of fibrinogen, immunoglobulin and complement in platelet activation promoted by *Staphylococcus aureus* clumping factor A. *Mol Microbiol* 57:804-818.
7. O'Brien L, Kerrigan S W, Kaw G., Hogan M., Penadés J., Litt D., Fitzgerald D. J., Foster T. J. & Cox D. (2002) Multiple mechanisms for the activation of human platelet aggregation by *Staphylococcus aureus*: roles for the clumping factors ClfA and ClfB, the serine-aspartate repeat protein SdrE and protein A. *Mol Microbiol* 44, 1033-1044.
8. Josefsson E., Hartford O., O'Brien L, Patti J M, Foster T (2001) Protection against experimental *Staphylococcus aureus* arthritis by vaccination with clumping factor A, a novel virulence determinant. *J Infect Dis* 184:1572-1580.
9. Palmqvist N, Foster T, Fitzgerald R, Josefsson E, Tarkowski A (2005) Fibronectin-binding proteins and fibrinogen-binding clumping factors play distinct roles in staphylococcal arthritis and systemic inflammation. *J Inf Dis* 191:791-798.
10. Deivanayagam C C S, Wann E R, Chen W, Carson M, Rajashankar K R, Höök M, Narayana S V L (2002) A novel variant of the immunoglobulin fold in surface adhesins of *Staphylococcus aureus*: crystal structure of the fibrinogen-binding MSCRAMM, clumping factor A. *The EMBO Journal* 21:6660-6672.
11. Bremell T, Lange S, Yacoub A, Ryden C, Tarkowski A (1991) Experimental *Staphylococcus aureus* arthritis in mice. *Infect Immun* 59:2615-2623.
12. Sakiniene E, Bremell T, Tarkowski A (1996) Addition of corticosteroids to antibiotic treatment ameliorates the course of experimental *Staphylococcus aureus* arthritis. *Arthritis Rheumatism* 39:1596-1605.
13. Verdrengh M, Tarkowski A (1997) Role of neutrophils in experimental septicemia and septic arthritis induced by *Staphylococcus aureus*. *Infect Immun* 65:2517-2521.
14. Duthie E S, Lorenz L L (1952) Staphylococcal coagulase: mode of action and antigenicity. *J Gen Microbiol* 6:95-107.
15. Kreiswirth B N, Löfdahl S, Betley M J, O'Reilly M, Schlievert P M, Bergdoll M S, Novick R P (1983) The toxic shock syndrome exotoxin structural gene is not detectably transmitted by a prophage. *Nature* 305:709-712.
16. Foster T J (1998) in *Methods in Microbiology Vol. 27: Bacterial Pathogenesis*, eds Williams P, Ketley J, Salmond G (Academic Press, London), pp 433-454.
17. O'Connell D P, Nanavaty T, McDevitt D, Gurusiddappa S, Höök M, Foster T J (1998) The fibrinogen-binding MSCRAMM (clumping factor) of *Staphylococcus aureus* has a $Ca^{2++}$-dependent inhibitory site. *J Biol Chem* 273: 6821-6829.
18. Sakiniene E, Bremell T, Tarkowski A (1999) Complement depletion aggravates *Staphylococcus aureus* septicaemia and septic arthritis. *Clin Exp Immunol* 115:95-102.
19. Mancini G, Carbonara A O, Heremans J F (1965) Immunochemical quantitation of antigens by single radial immunodiffusion. *Immunochemistry* 2:235-254.
20. Bremell T, Abdelnour A, Tarkowski A (1992) Histopathological and serological progression of experimental *Staphylococcus aureus* arthritis. *Infect Immun* 60:2976-2985.

```
                    SEQUENCE LISTING

<160> NUMBER OF SEQ ID NOS: 14

<210> SEQ ID NO 1
<211> LENGTH: 933
<212> TYPE: PRT
<213> ORGANISM: Artificial
<220> FEATURE:
<223> OTHER INFORMATION: recombinant ClfA (wild type) full length
      protein sequence

<400> SEQUENCE: 1

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Phe Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190
```

```
Ser Thr Asp Ala Ser Asn Lys Asp Val Val Asn Gln Ala Val Asn Thr
            195                 200                 205
Ser Ala Pro Arg Met Arg Ala Phe Ser Leu Ala Ala Val Ala Ala Asp
            210                 215                 220
Ala Pro Ala Ala Gly Thr Asp Ile Thr Asn Gln Leu Thr Asn Val Thr
225                 230                 235                 240
Val Gly Ile Asp Ser Gly Thr Thr Val Tyr Pro His Gln Ala Gly Tyr
                245                 250                 255
Val Lys Leu Asn Tyr Gly Phe Ser Val Pro Asn Ser Ala Val Lys Gly
                260                 265                 270
Asp Thr Phe Lys Ile Thr Val Pro Lys Glu Leu Asn Leu Asn Gly Val
            275                 280                 285
Thr Ser Thr Ala Lys Val Pro Pro Ile Met Ala Gly Asp Gln Val Leu
            290                 295                 300
Ala Asn Gly Val Ile Asp Ser Asp Gly Asn Val Ile Tyr Thr Phe Thr
305                 310                 315                 320
Asp Tyr Val Asn Thr Lys Asp Val Lys Ala Thr Leu Thr Met Pro
                325                 330                 335
Ala Tyr Ile Asp Pro Glu Asn Val Lys Lys Thr Gly Asn Val Thr Leu
                340                 345                 350
Ala Thr Gly Ile Gly Ser Thr Thr Ala Asn Lys Thr Val Leu Val Asp
            355                 360                 365
Tyr Glu Lys Tyr Gly Lys Phe Tyr Asn Leu Ser Ile Lys Gly Thr Ile
            370                 375                 380
Asp Gln Ile Asp Lys Thr Asn Asn Thr Tyr Arg Gln Thr Ile Tyr Val
385                 390                 395                 400
Asn Pro Ser Gly Asp Asn Val Ile Ala Pro Val Leu Thr Gly Asn Leu
                405                 410                 415
Lys Pro Asn Thr Asp Ser Asn Ala Leu Ile Asp Gln Gln Asn Thr Ser
            420                 425                 430
Ile Lys Val Tyr Lys Val Asp Asn Ala Ala Asp Leu Ser Glu Ser Tyr
            435                 440                 445
Phe Val Asn Pro Glu Asn Phe Glu Asp Val Thr Asn Ser Val Asn Ile
450                 455                 460
Thr Phe Pro Asn Pro Asn Gln Tyr Lys Val Glu Phe Asn Thr Pro Asp
465                 470                 475                 480
Asp Gln Ile Thr Thr Pro Tyr Ile Val Val Asn Gly His Ile Asp
                485                 490                 495
Pro Asn Ser Lys Gly Asp Leu Ala Leu Arg Ser Thr Leu Tyr Gly Tyr
                500                 505                 510
Asn Ser Asn Ile Ile Trp Arg Ser Met Ser Trp Asp Asn Glu Val Ala
            515                 520                 525
Phe Asn Asn Gly Ser Gly Ser Gly Asp Gly Ile Asp Lys Pro Val Val
            530                 535                 540
Pro Glu Gln Pro Asp Glu Pro Gly Glu Ile Pro Ile Pro Glu Asp
545                 550                 555                 560
Ser Asp Ser Asp Pro Gly Ser Asp Ser Gly Ser Asp Ser Asn Ser Asp
                565                 570                 575
Ser Gly Ser Asp Ser Gly Ser Asp Ser Thr Ser Asp Ser Gly Ser Asp
            580                 585                 590
Ser Ala Ser Asp Ser Asp Ser Ala Ser Asp Ser Asp Ser Ala Ser Asp
            595                 600                 605
Ser Asp Ser Ala Ser Asp Ser Asp Ser Ala Ser Asp Ser Asp Ser Asp
```

```
                        610                 615                 620
Asn Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp Ser Asp
                645                 650                 655

Ser Asp Ser Asp Ser Asp Ser Asp Ser Asp Ser Asp Ser Asp Ser Asp
            660                 665                 670

Ser Asp Ser Asp Ser Asp Ser Asp Ser Asp Ser Asp Ser Asp Ser Asp
        675                 680                 685

Ser Asp Ser Asp Ser Asp Ser Asp Ser Asp Ser Asp Ser Asp Ser Asp
    690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                725                 730                 735

Ser Asp Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Asp Ser Ala
        755                 760                 765

Ser Asp Ser Asp Ser Asp Ser Asp Ser Asp Ser Asp Ser Asp Ser Asp
    770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Glu Ser Asp
                805                 810                 815

Ser Asp Ser Asp Ser Asp Ser Asp Ser Asp Ser Asp Ser Asp Ser Asp
            820                 825                 830

Ser Asp Ser Asp Ser Ala Ser Asp Ser Asp Ser Gly Ser Asp Ser Asp
        835                 840                 845

Ser Ser Ser Asp Ser Asp Ser Glu Ser Asp Ser Asn Ser Asp Ser Glu
    850                 855                 860

Ser Gly Ser Asn Asn Asn Val Val Pro Pro Asn Ser Pro Lys Asn Gly
865                 870                 875                 880

Thr Asn Ala Ser Asn Lys Asn Glu Ala Lys Asp Ser Lys Glu Pro Leu
                885                 890                 895

Pro Asp Thr Gly Ser Glu Asp Glu Ala Asn Thr Ser Leu Ile Trp Gly
            900                 905                 910

Leu Leu Ala Ser Ile Gly Ser Leu Leu Leu Phe Arg Arg Lys Lys Glu
        915                 920                 925

Asn Lys Asp Lys Lys
    930

<210> SEQ ID NO 2
<211> LENGTH: 1560
<212> TYPE: DNA
<213> ORGANISM: Artificial
<220> FEATURE:
<223> OTHER INFORMATION: recombinant ClfA A domain (wild type) Regions
      N1 N2 N3
<220> FEATURE:
<221> NAME/KEY: CDS
<222> LOCATION: (1)..(1560)

<400> SEQUENCE: 2 agt gaa aat agt gtt acg caa tct gat agc gca agt aac gaa agc aaa      48
Ser Glu Asn Ser Val Thr Gln Ser Asp Ser Ala Ser Asn Glu Ser Lys
1               5                   10                  15
```

```
agt aat gat tca agt agc gtt agt gct gca cct aaa aca gac gac aca     96
Ser Asn Asp Ser Ser Ser Val Ser Ala Ala Pro Lys Thr Asp Asp Thr
         20                  25                  30 aac gtg agt gat act aaa aca tcg tca aac act aat aat ggc gaa acg    144
Asn Val Ser Asp Thr Lys Thr Ser Ser Asn Thr Asn Asn Gly Glu Thr
     35                  40                  45 agt gtg gcg caa aat cca gca caa cag gaa acg aca caa tca tca tca    192
Ser Val Ala Gln Asn Pro Ala Gln Gln Glu Thr Thr Gln Ser Ser Ser
 50                  55                  60 aca aat gca act acg gaa gaa acg ccg gta act ggt gaa gct act act    240
Thr Asn Ala Thr Thr Glu Glu Thr Pro Val Thr Gly Glu Ala Thr Thr
 65                  70                  75                  80 acg aca acg aat caa gct aat aca ccg gca aca act caa tca agc aat    288
Thr Thr Thr Asn Gln Ala Asn Thr Pro Ala Thr Thr Gln Ser Ser Asn
                 85                  90                  95 aca aat gcg gag gaa tta gtg aat caa aca agt aat gaa acg act ttt    336
Thr Asn Ala Glu Glu Leu Val Asn Gln Thr Ser Asn Glu Thr Thr Phe
            100                 105                 110 aat gat act aat aca gta tca tct gta aat tca cct caa aat tct aca    384
Asn Asp Thr Asn Thr Val Ser Ser Val Asn Ser Pro Gln Asn Ser Thr
        115                 120                 125 aat gcg gaa aat gtt tca aca acg caa gat act tca act gaa gca aca    432
Asn Ala Glu Asn Val Ser Thr Thr Gln Asp Thr Ser Thr Glu Ala Thr
130                 135                 140 cct tca aac aat gaa tca gct cca cag agt aca gat gca agt aat aaa    480
Pro Ser Asn Asn Glu Ser Ala Pro Gln Ser Thr Asp Ala Ser Asn Lys
145                 150                 155                 160 gat gta gtt aat caa gcg gtt aat aca agt gcg cct aga atg aga gca    528
Asp Val Val Asn Gln Ala Val Asn Thr Ser Ala Pro Arg Met Arg Ala
                165                 170                 175 ttt agt tta gcg gca gta gct gca gat gca ccg gca gct ggc aca gat    576
Phe Ser Leu Ala Ala Val Ala Ala Asp Ala Pro Ala Ala Gly Thr Asp
            180                 185                 190 att acg aat cag ttg acg aat gtg aca gtt ggt att gac tct ggt acg    624
Ile Thr Asn Gln Leu Thr Asn Val Thr Val Gly Ile Asp Ser Gly Thr
        195                 200                 205 act gtg tat ccg cac caa gca ggt tat gtc aaa ctg aat tat ggt ttt    672
Thr Val Tyr Pro His Gln Ala Gly Tyr Val Lys Leu Asn Tyr Gly Phe
210                 215                 220 tca gtg cct aat tct gct gtt aaa ggt gac aca ttc aaa ata act gta    720
Ser Val Pro Asn Ser Ala Val Lys Gly Asp Thr Phe Lys Ile Thr Val
225                 230                 235                 240 cct aaa gaa tta aac tta aat ggt gta act tca act gct aaa gtg cca    768
Pro Lys Glu Leu Asn Leu Asn Gly Val Thr Ser Thr Ala Lys Val Pro
                245                 250                 255 cca att atg gct gga gat caa gta ttg gca aat ggt gta atc gat agt    816
Pro Ile Met Ala Gly Asp Gln Val Leu Ala Asn Gly Val Ile Asp Ser
            260                 265                 270 gat ggt aat gtt att tat aca ttt aca gac tat gta aat act aaa gat    864
Asp Gly Asn Val Ile Tyr Thr Phe Thr Asp Tyr Val Asn Thr Lys Asp
        275                 280                 285 gat gta aaa gca act ttg acc atg ccc gct tat att gac cct gaa aat    912
Asp Val Lys Ala Thr Leu Thr Met Pro Ala Tyr Ile Asp Pro Glu Asn
290                 295                 300 gtt aaa aag aca ggt aat gtg aca ttg gct act ggc ata ggt agt aca    960
Val Lys Lys Thr Gly Asn Val Thr Leu Ala Thr Gly Ile Gly Ser Thr
305                 310                 315                 320 aca gca aac aaa aca gta tta gta gat tat gaa aaa tat ggt aag ttt   1008
Thr Ala Asn Lys Thr Val Leu Val Asp Tyr Glu Lys Tyr Gly Lys Phe
```

-continued

```
                    325                 330                 335
tat aac tta tct att aaa ggt aca att gac caa atc gat aaa aca aat    1056
Tyr Asn Leu Ser Ile Lys Gly Thr Ile Asp Gln Ile Asp Lys Thr Asn
            340                 345                 350 aat acg tat cgt cag aca att tat gtc aat cca agt gga gat aac gtt    1104
Asn Thr Tyr Arg Gln Thr Ile Tyr Val Asn Pro Ser Gly Asp Asn Val
        355                 360                 365 att gcg ccg gtt tta aca ggt aat tta aaa cca aat acg gat agt aat    1152
Ile Ala Pro Val Leu Thr Gly Asn Leu Lys Pro Asn Thr Asp Ser Asn
    370                 375                 380 gca tta ata gat cag caa aat aca agt att aaa gta tat aaa gta gat    1200
Ala Leu Ile Asp Gln Gln Asn Thr Ser Ile Lys Val Tyr Lys Val Asp
385                 390                 395                 400 aat gca gct gat tta tct gaa agt tac ttt gtg aat cca gaa aac ttt    1248
Asn Ala Ala Asp Leu Ser Glu Ser Tyr Phe Val Asn Pro Glu Asn Phe
                405                 410                 415 gag gat gtc act aat agt gtg aat att aca ttc cca aat cca aat caa    1296
Glu Asp Val Thr Asn Ser Val Asn Ile Thr Phe Pro Asn Pro Asn Gln
            420                 425                 430 tat aaa gta gag ttt aat acg cct gat gat caa att aca aca ccg tat    1344
Tyr Lys Val Glu Phe Asn Thr Pro Asp Asp Gln Ile Thr Thr Pro Tyr
        435                 440                 445 ata gta gtt gtt aat ggt cat att gat ccg aat agc aaa ggt gat tta    1392
Ile Val Val Val Asn Gly His Ile Asp Pro Asn Ser Lys Gly Asp Leu
    450                 455                 460 gct tta cgt tca act tta tat ggg tat aac tcg aat ata att tgg cgc    1440
Ala Leu Arg Ser Thr Leu Tyr Gly Tyr Asn Ser Asn Ile Ile Trp Arg
465                 470                 475                 480 tct atg tca tgg gac aac gaa gta gca ttt aat aac gga tca ggt tct    1488
Ser Met Ser Trp Asp Asn Glu Val Ala Phe Asn Asn Gly Ser Gly Ser
                485                 490                 495 ggt gac ggt atc gat aaa cca gtt gtt cct gaa caa cct gat gag cct    1536
Gly Asp Gly Ile Asp Lys Pro Val Val Pro Glu Gln Pro Asp Glu Pro
            500                 505                 510 ggt gaa att gaa cca att cca gag                                    1560
Gly Glu Ile Glu Pro Ile Pro Glu
        515                 520

<210> SEQ ID NO 3
<211> LENGTH: 520
<212> TYPE: PRT
<213> ORGANISM: Artificial
<220> FEATURE:
<223> OTHER INFORMATION: Synthetic Construct

<400> SEQUENCE: 3

Ser Glu Asn Ser Val Thr Gln Ser Asp Ser Ala Ser Asn Glu Ser Lys
1               5                   10                  15

Ser Asn Asp Ser Ser Val Ser Ala Ala Pro Lys Thr Asp Asp Thr
            20                  25                  30

Asn Val Ser Asp Thr Lys Thr Ser Ser Asn Thr Asn Asn Gly Glu Thr
        35                  40                  45

Ser Val Ala Gln Asn Pro Ala Gln Gln Glu Thr Thr Gln Ser Ser Ser
    50                  55                  60

Thr Asn Ala Thr Thr Glu Thr Pro Val Thr Gly Glu Ala Thr Thr
65                  70                  75                  80

Thr Thr Thr Asn Gln Ala Asn Thr Pro Ala Thr Thr Gln Ser Ser Asn
                85                  90                  95

Thr Asn Ala Glu Glu Leu Val Asn Gln Thr Ser Asn Glu Thr Thr Phe
```

```
                100                 105                 110
Asn Asp Thr Asn Thr Val Ser Ser Val Asn Ser Pro Gln Asn Ser Thr
            115                 120                 125
Asn Ala Glu Asn Val Ser Thr Thr Gln Asp Thr Ser Thr Glu Ala Thr
        130                 135                 140
Pro Ser Asn Asn Glu Ser Ala Pro Gln Ser Thr Asp Ala Ser Asn Lys
145                 150                 155                 160
Asp Val Val Asn Gln Ala Val Asn Thr Ser Ala Pro Arg Met Arg Ala
                165                 170                 175
Phe Ser Leu Ala Ala Val Ala Ala Asp Ala Pro Ala Ala Gly Thr Asp
            180                 185                 190
Ile Thr Asn Gln Leu Thr Asn Val Thr Val Gly Ile Asp Ser Gly Thr
        195                 200                 205
Thr Val Tyr Pro His Gln Ala Gly Tyr Val Lys Leu Asn Tyr Gly Phe
    210                 215                 220
Ser Val Pro Asn Ser Ala Val Lys Gly Asp Thr Phe Lys Ile Thr Val
225                 230                 235                 240
Pro Lys Glu Leu Asn Leu Asn Gly Val Thr Ser Thr Ala Lys Val Pro
                245                 250                 255
Pro Ile Met Ala Gly Asp Gln Val Leu Ala Asn Gly Val Ile Asp Ser
            260                 265                 270
Asp Gly Asn Val Ile Tyr Thr Phe Thr Asp Tyr Val Asn Thr Lys Asp
        275                 280                 285
Asp Val Lys Ala Thr Leu Thr Met Pro Ala Tyr Ile Asp Pro Glu Asn
    290                 295                 300
Val Lys Lys Thr Gly Asn Val Thr Leu Ala Thr Gly Ile Gly Ser Thr
305                 310                 315                 320
Thr Ala Asn Lys Thr Val Leu Val Asp Tyr Glu Lys Tyr Gly Lys Phe
                325                 330                 335
Tyr Asn Leu Ser Ile Lys Gly Thr Ile Asp Gln Ile Asp Lys Thr Asn
            340                 345                 350
Asn Thr Tyr Arg Gln Thr Ile Tyr Val Asn Pro Ser Gly Asp Asn Val
        355                 360                 365
Ile Ala Pro Val Leu Thr Gly Asn Leu Lys Pro Asn Thr Asp Ser Asn
    370                 375                 380
Ala Leu Ile Asp Gln Gln Asn Thr Ser Ile Lys Val Tyr Lys Val Asp
385                 390                 395                 400
Asn Ala Ala Asp Leu Ser Glu Ser Tyr Phe Val Asn Pro Glu Asn Phe
                405                 410                 415
Glu Asp Val Thr Asn Ser Val Asn Ile Thr Phe Pro Asn Pro Asn Gln
            420                 425                 430
Tyr Lys Val Glu Phe Asn Thr Pro Asp Asp Gln Ile Thr Thr Pro Tyr
        435                 440                 445
Ile Val Val Val Asn Gly His Ile Asp Pro Asn Ser Lys Gly Asp Leu
    450                 455                 460
Ala Leu Arg Ser Thr Leu Tyr Gly Tyr Asn Ser Asn Ile Ile Trp Arg
465                 470                 475                 480
Ser Met Ser Trp Asp Asn Glu Val Ala Phe Asn Asn Gly Ser Gly Ser
                485                 490                 495
Gly Asp Gly Ile Asp Lys Pro Val Val Pro Glu Gln Pro Asp Glu Pro
            500                 505                 510
Gly Glu Ile Glu Pro Ile Pro Glu
        515                 520
```

-continued

```
<210> SEQ ID NO 4
<211> LENGTH: 520
<212> TYPE: PRT
<213> ORGANISM: Artificial
<220> FEATURE:
<223> OTHER INFORMATION: ClfA A domain Regions N1 N2 N3 with alterations
      (ClfA P336S Y338A)

<400> SEQUENCE:

```
                355                 360                 365
Ile Ala Pro Val Leu Thr Gly Asn Leu Lys Pro Asn Thr Asp Ser Asn
370                 375                 380

Ala Leu Ile Asp Gln Gln Asn Thr Ser Ile Lys Val Tyr Lys Val Asp
385                 390                 395                 400

Asn Ala Ala Asp Leu Ser Glu Ser Tyr Phe Val Asn Pro Glu Asn Phe
                405                 410                 415

Glu Asp Val Thr Asn Ser Val Asn Ile Thr Phe Pro Asn Pro Asn Gln
                420                 425                 430

Tyr Lys Val Glu Phe Asn Thr Pro Asp Asp Gln Ile Thr Thr Pro Tyr
                435                 440                 445

Ile Val Val Val Asn Gly His Ile Asp Pro Asn Ser Lys Gly Asp Leu
                450                 455                 460

Ala Leu Arg Ser Thr Leu Tyr Gly Tyr Asn Ser Asn Ile Ile Trp Arg
465                 470                 475                 480

Ser Met Ser Trp Asp Asn Glu Val Ala Phe Asn Asn Gly Ser Gly Ser
                485                 490                 495

Gly Asp Gly Ile Asp Lys Pro Val Val Pro Glu Gln Pro Asp Glu Pro
                500                 505                 510

Gly Glu Ile Glu Pro Ile Pro Glu
                515                 520

<210> SEQ ID NO 5
<211> LENGTH: 520
<212> TYPE: PRT
<213> ORGANISM: Artificial
<220> FEATURE:
<223> OTHER INFORMATION: ClfA A domain Regions N1 N2 N3 with alterations
      (ClfA P336A Y338S)

<400> SEQUENCE: 5

Ser Glu Asn Ser Val Thr Gln Ser Asp Ser Ala Ser Asn Glu Ser Lys
1               5                   10                  15

Ser Asn Asp Ser Ser Ser Val Ser Ala Ala Pro Lys Thr Asp Asp Thr
                20                  25                  30

Asn Val Ser Asp Thr Lys Thr Ser Ser Asn Thr Asn Asn Gly Glu Thr
                35                  40                  45

Ser Val Ala Gln Asn Pro Ala Gln Gln Glu Thr Thr Gln Ser Ser Ser
                50                  55                  60

Thr Asn Ala Thr Thr Glu Glu Thr Pro Val Thr Gly Glu Ala Thr Thr
65                  70                  75                  80

Thr Thr Thr Asn Gln Ala Asn Thr Pro Ala Thr Thr Gln Ser Ser Asn
                85                  90                  95

Thr Asn Ala Glu Glu Leu Val Asn Gln Thr Ser Asn Glu Thr Thr Phe
                100                 105                 110

Asn Asp Thr Asn Thr Val Ser Ser Val Asn Ser Pro Gln Asn Ser Thr
                115                 120                 125

Asn Ala Glu Asn Val Ser Thr Thr Gln Asp Thr Ser Thr Glu Ala Thr
                130                 135                 140

Pro Ser Asn Asn Glu Ser Ala Pro Gln Ser Thr Asp Ala Ser Asn Lys
145                 150                 155                 160

Asp Val Val Asn Gln Ala Val Asn Thr Ser Ala Pro Arg Met Arg Ala
                165                 170                 175

Phe Ser Leu Ala Ala Val Ala Ala Asp Ala Pro Ala Ala Gly Thr Asp
                180                 185                 190
```

```
Ile Thr Asn Gln Leu Thr Asn Val Thr Val Gly Ile Asp Ser Gly Thr
        195                 200                 205

Thr Val Tyr Pro His Gln Ala Gly Tyr Val Lys Leu Asn Tyr Gly Phe
    210                 215                 220

Ser Val Pro Asn Ser Ala Val Lys Gly Asp Thr Phe Lys Ile Thr Val
225                 230                 235                 240

Pro Lys Glu Leu Asn Leu Asn Gly Val Thr Ser Thr Ala Lys Val Pro
                245                 250                 255

Pro Ile Met Ala Gly Asp Gln Val Leu Ala Asn Gly Val Ile Asp Ser
            260                 265                 270

Asp Gly Asn Val Ile Tyr Thr Phe Thr Asp Tyr Val Asn Thr Lys Asp
        275                 280                 285

Asp Val Lys Ala Thr Leu Thr Met Ala Ala Ser Ile Asp Pro Glu Asn
    290                 295                 300

Val Lys Lys Thr Gly Asn Val Thr Leu Ala Thr Gly Ile Gly Ser Thr
305                 310                 315                 320

Thr Ala Asn Lys Thr Val Leu Val Asp Tyr Glu Lys Tyr Gly Lys Phe
                325                 330                 335

Tyr Asn Leu Ser Ile Lys Gly Thr Ile Asp Gln Ile Asp Lys Thr Asn
            340                 345                 350

Asn Thr Tyr Arg Gln Thr Ile Tyr Val Asn Pro Ser Gly Asp Asn Val
        355                 360                 365

Ile Ala Pro Val Leu Thr Gly Asn Leu Lys Pro Asn Thr Asp Ser Asn
    370                 375                 380

Ala Leu Ile Asp Gln Gln Asn Thr Ser Ile Lys Val Tyr Lys Val Asp
385                 390                 395                 400

Asn Ala Ala Asp Leu Ser Glu Ser Tyr Phe Val Asn Pro Glu Asn Phe
                405                 410                 415

Glu Asp Val Thr Asn Ser Val Asn Ile Thr Phe Pro Asn Pro Asn Gln
            420                 425                 430

Tyr Lys Val Glu Phe Asn Thr Pro Asp Asp Gln Ile Thr Thr Pro Tyr
        435                 440                 445

Ile Val Val Val Asn Gly His Ile Asp Pro Asn Ser Lys Gly Asp Leu
    450                 455                 460

Ala Leu Arg Ser Thr Leu Tyr Gly Tyr Asn Ser Asn Ile Ile Trp Arg
465                 470                 475                 480

Ser Met Ser Trp Asp Asn Glu Val Ala Phe Asn Asn Gly Ser Gly Ser
                485                 490                 495

Gly Asp Gly Ile Asp Lys Pro Val Val Pro Glu Gln Pro Asp Glu Pro
            500                 505                 510

Gly Glu Ile Glu Pro Ile Pro Glu
        515                 520

<210> SEQ ID NO 6
<211> LENGTH: 530
<212> TYPE: PRT
<213> ORGANISM: ARTIFICIAL
<220> FEATURE:
<223> OTHER INFORMATION: wt rClfA A region with additional N and C
      terminal residues

<400> SEQUENCE: 6

His His His His His Gly Ser Ser Glu Asn Ser Val Thr Gln Ser
1               5                   10                  15

Asp Ser Ala Ser Asn Glu Ser Lys Ser Asn Asp Ser Ser Val Ser
                20                  25                  30
```

```
Ala Ala Pro Lys Thr Asp Asp Thr Asn Val Ser Asp Thr Lys Thr Ser
         35                  40                  45

Ser Asn Thr Asn Asn Gly Glu Thr Ser Val Ala Gln Asn Pro Ala Gln
     50                  55                  60

Gln Glu Thr Thr Gln Ser Ser Ser Thr Asn Ala Thr Thr Glu Glu Thr
 65                  70                  75                  80

Pro Val Thr Gly Glu Ala Thr Thr Thr Thr Asn Gln Ala Asn Thr
                 85                  90                  95

Pro Ala Thr Thr Gln Ser Ser Asn Thr Asn Ala Glu Glu Leu Val Asn
                100                 105                 110

Gln Thr Ser Asn Glu Thr Thr Phe Asn Asp Thr Asn Thr Val Ser Ser
             115                 120                 125

Val Asn Ser Pro Gln Asn Ser Thr Asn Ala Glu Asn Val Ser Thr Thr
         130                 135                 140

Gln Asp Thr Ser Thr Glu Ala Thr Pro Ser Asn Asn Glu Ser Ala Pro
145                 150                 155                 160

Gln Ser Thr Asp Ala Ser Asn Lys Asp Val Val Asn Gln Ala Val Asn
                 165                 170                 175

Thr Ser Ala Pro Arg Met Arg Ala Phe Ser Leu Ala Ala Val Ala Ala
                 180                 185                 190

Asp Ala Pro Ala Ala Gly Thr Asp Ile Thr Asn Gln Leu Thr Asn Val
             195                 200                 205

Thr Val Gly Ile Asp Ser Gly Thr Thr Val Tyr Pro His Gln Ala Gly
         210                 215                 220

Tyr Val Lys Leu Asn Tyr Gly Phe Ser Val Pro Asn Ser Ala Val Lys
225                 230                 235                 240

Gly Asp Thr Phe Lys Ile Thr Val Pro Lys Glu Leu Asn Leu Asn Gly
                 245                 250                 255

Val Thr Ser Thr Ala Lys Val Pro Pro Ile Met Ala Gly Asp Gln Val
             260                 265                 270

Leu Ala Asn Gly Val Ile Asp Ser Asp Gly Asn Val Ile Tyr Thr Phe
         275                 280                 285

Thr Asp Tyr Val Asn Thr Lys Asp Asp Val Lys Ala Thr Leu Thr Met
290                 295                 300

Pro Ala Tyr Ile Asp Pro Glu Asn Val Lys Lys Thr Gly Asn Val Thr
305                 310                 315                 320

Leu Ala Thr Gly Ile Gly Ser Thr Thr Ala Asn Lys Thr Val Leu Val
                 325                 330                 335

Asp Tyr Glu Lys Tyr Gly Lys Phe Tyr Asn Leu Ser Ile Lys Gly Thr
             340                 345                 350

Ile Asp Gln Ile Asp Lys Thr Asn Asn Thr Tyr Arg Gln Thr Ile Tyr
         355                 360                 365

Val Asn Pro Ser Gly Asp Asn Val Ile Ala Pro Val Leu Thr Gly Asn
     370                 375                 380

Leu Lys Pro Asn Thr Asp Ser Asn Ala Leu Ile Asp Gln Gln Asn Thr
385                 390                 395                 400

Ser Ile Lys Val Tyr Lys Val Asp Asn Ala Ala Asp Leu Ser Glu Ser
                 405                 410                 415

Tyr Phe Val Asn Pro Glu Asn Phe Glu Asp Val Thr Asn Ser Val Asn
             420                 425                 430

Ile Thr Phe Pro Asn Pro Asn Gln Tyr Lys Val Glu Phe Asn Thr Pro
         435                 440                 445
```

```
Asp Asp Gln Ile Thr Thr Pro Tyr Ile Val Val Asn Gly His Ile
    450                 455                 460
Asp Pro Asn Ser Lys Gly Asp Leu Ala Leu Arg Ser Thr Leu Tyr Gly
465                 470                 475                 480
Tyr Asn Ser Asn Ile Ile Trp Arg Ser Met Ser Trp Asp Asn Glu Val
                485                 490                 495
Ala Phe Asn Asn Gly Ser Gly Ser Gly Asp Gly Ile Asp Lys Pro Val
                500                 505                 510
Val Pro Glu Gln Pro Asp Glu Pro Gly Glu Ile Glu Pro Ile Pro Glu
        515                 520                 525
Lys Leu
    530

<210> SEQ ID NO 7
<211> LENGTH: 530
<212> TYPE: PRT
<213> ORGANISM: ARTIFICIAL
<220> FEATURE:
<223> OTHER INFORMATION: wt rClfAPYI A region with additional N and C
      terminal residues

<400> SEQUENCE: 7

His His His His His His Gly Ser Ser Glu Asn Ser Val Thr Gln Ser
1               5                   10                  15
Asp Ser Ala Ser Asn Glu Ser Lys Ser Asn Asp Ser Ser Val Ser
            20                  25                  30
Ala Ala Pro Lys Thr Asp Asp Thr Asn Val Ser Asp Thr Lys Thr Ser
            35                  40                  45
Ser Asn Thr Asn Asn Gly Glu Thr Ser Val Ala Gln Asn Pro Ala Gln
    50                  55                  60
Gln Glu Thr Thr Gln Ser Ser Ser Thr Asn Ala Thr Thr Glu Glu Thr
65                  70                  75                  80
Pro Val Thr Gly Glu Ala Thr Thr Thr Thr Asn Gln Ala Asn Thr
                85                  90                  95
Pro Ala Thr Thr Gln Ser Ser Asn Thr Asn Ala Glu Glu Leu Val Asn
                100                 105                 110
Gln Thr Ser Asn Glu Thr Thr Phe Asn Asp Thr Asn Thr Val Ser Ser
            115                 120                 125
Val Asn Ser Pro Gln Asn Ser Thr Asn Ala Glu Asn Val Ser Thr Thr
    130                 135                 140
Gln Asp Thr Ser Thr Glu Ala Thr Pro Ser Asn Asn Glu Ser Ala Pro
145                 150                 155                 160
Gln Ser Thr Asp Ala Ser Asn Lys Asp Val Val Asn Gln Ala Val Asn
                165                 170                 175
Thr Ser Ala Pro Arg Met Arg Ala Phe Ser Leu Ala Ala Val Ala Ala
                180                 185                 190
Asp Ala Pro Ala Ala Gly Thr Asp Ile Thr Asn Gln Leu Thr Asn Val
            195                 200                 205
Thr Val Gly Ile Asp Ser Gly Thr Thr Val Tyr Pro His Gln Ala Gly
    210                 215                 220
Tyr Val Lys Leu Asn Tyr Gly Phe Ser Val Pro Asn Ser Ala Val Lys
225                 230                 235                 240
Gly Asp Thr Phe Lys Ile Thr Val Pro Lys Glu Leu Asn Leu Asn Gly
                245                 250                 255
Val Thr Ser Thr Ala Lys Val Pro Pro Ile Met Ala Gly Asp Gln Val
                260                 265                 270
```

-continued

```
Leu Ala Asn Gly Val Ile Asp Ser Asp Gly Asn Val Ile Tyr Thr Phe
            275                 280                 285

Thr Asp Tyr Val Asn Thr Lys Asp Asp Val Lys Ala Thr Leu Thr Met
290                 295                 300

Ser Ala Ala Ile Asp Pro Glu Asn Val Lys Lys Thr Gly Asn Val Thr
305                 310                 315                 320

Leu Ala Thr Gly Ile Gly Ser Thr Thr Ala Asn Lys Thr Val Leu Val
                325                 330                 335

Asp Tyr Glu Lys Tyr Gly Lys Phe Tyr Asn Leu Ser Ile Lys Gly Thr
            340                 345                 350

Ile Asp Gln Ile Asp Lys Thr Asn Asn Thr Tyr Arg Gln Thr Ile Tyr
                355                 360                 365

Val Asn Pro Ser Gly Asp Asn Val Ile Ala Pro Val Leu Thr Gly Asn
370                 375                 380

Leu Lys Pro Asn Thr Asp Ser Asn Ala Leu Ile Asp Gln Gln Asn Thr
385                 390                 395                 400

Ser Ile Lys Val Tyr Lys Val Asp Asn Ala Ala Asp Leu Ser Glu Ser
                405                 410                 415

Tyr Phe Val Asn Pro Glu Asn Phe Glu Asp Val Thr Asn Ser Val Asn
            420                 425                 430

Ile Thr Phe Pro Asn Pro Asn Gln Tyr Lys Val Glu Phe Asn Thr Pro
                435                 440                 445

Asp Asp Gln Ile Thr Thr Pro Tyr Ile Val Val Asn Gly His Ile
450                 455                 460

Asp Pro Asn Ser Lys Gly Asp Leu Ala Leu Arg Ser Thr Leu Tyr Gly
465                 470                 475                 480

Tyr Asn Ser Asn Ile Ile Trp Arg Ser Met Ser Trp Asp Asn Glu Val
                485                 490                 495

Ala Phe Asn Asn Gly Ser Gly Ser Gly Asp Gly Ile Asp Lys Pro Val
            500                 505                 510

Val Pro Glu Gln Pro Asp Glu Pro Gly Glu Ile Glu Pro Ile Pro Glu
                515                 520                 525

Lys Leu
    530
```

<210> SEQ ID NO 8
<211> LENGTH: 530
<212> TYPE: PRT
<213> ORGANISM: ARTIFICIAL
<220> FEATURE:
<223> OTHER INFORMATION: wt rClfAPYII A region with additional N and C
      terminal residues

<400> SEQUENCE: 8

```
His His His His His His Gly Ser Ser Glu Asn Ser Val Thr Gln Ser
1               5                   10                  15

Asp Ser Ala Ser Asn Glu Ser Lys Ser Asn Asp Ser Ser Val Ser
            20                  25                  30

Ala Ala Pro Lys Thr Asp Asp Thr Asn Val Ser Asp Thr Lys Thr Ser
                35                  40                  45

Ser Asn Thr Asn Asn Gly Glu Thr Ser Val Ala Gln Asn Pro Ala Gln
            50                  55                  60

Gln Glu Thr Thr Gln Ser Ser Ser Thr Asn Ala Thr Thr Glu Glu Thr
65                  70                  75                  80

Pro Val Thr Gly Glu Ala Thr Thr Thr Thr Thr Asn Gln Ala Asn Thr
```

```
                         85                    90                        95
Pro Ala Thr Thr Gln Ser Ser Asn Thr Asn Ala Glu Glu Leu Val Asn
                100                     105                 110

Gln Thr Ser Asn Glu Thr Thr Phe Asn Asp Thr Asn Thr Val Ser Ser
            115                     120                 125

Val Asn Ser Pro Gln Asn Ser Thr Asn Ala Glu Asn Val Ser Thr Thr
        130                     135                 140

Gln Asp Thr Ser Thr Glu Ala Thr Pro Ser Asn Asn Glu Ser Ala Pro
145                     150                 155                 160

Gln Ser Thr Asp Ala Ser Asn Lys Asp Val Val Asn Gln Ala Val Asn
                165                 170                 175

Thr Ser Ala Pro Arg Met Arg Ala Phe Ser Leu Ala Ala Val Ala Ala
                180                 185                 190

Asp Ala Pro Ala Ala Gly Thr Asp Ile Thr Asn Gln Leu Thr Asn Val
                195                 200                 205

Thr Val Gly Ile Asp Ser Gly Thr Thr Val Tyr Pro His Gln Ala Gly
        210                     215                 220

Tyr Val Lys Leu Asn Tyr Gly Phe Ser Val Pro Asn Ser Ala Val Lys
225                     230                 235                 240

Gly Asp Thr Phe Lys Ile Thr Val Pro Lys Glu Leu Asn Leu Asn Gly
                245                 250                 255

Val Thr Ser Thr Ala Lys Val Pro Pro Ile Met Ala Gly Asp Gln Val
                260                 265                 270

Leu Ala Asn Gly Val Ile Asp Ser Asp Gly Asn Val Ile Tyr Thr Phe
                275                 280                 285

Thr Asp Tyr Val Asn Thr Lys Asp Asp Val Lys Ala Thr Leu Thr Met
        290                     295                 300

Ala Ala Ser Ile Asp Pro Glu Asn Val Lys Lys Thr Gly Asn Val Thr
305                     310                 315                 320

Leu Ala Thr Gly Ile Gly Ser Thr Thr Ala Asn Lys Thr Val Leu Val
                325                 330                 335

Asp Tyr Glu Lys Tyr Gly Lys Phe Tyr Asn Leu Ser Ile Lys Gly Thr
                340                 345                 350

Ile Asp Gln Ile Asp Lys Thr Asn Asn Thr Tyr Arg Gln Thr Ile Tyr
        355                     360                 365

Val Asn Pro Ser Gly Asp Asn Val Ile Ala Pro Val Leu Thr Gly Asn
        370                     375                 380

Leu Lys Pro Asn Thr Asp Ser Asn Ala Leu Ile Asp Gln Gln Asn Thr
385                     390                 395                 400

Ser Ile Lys Val Tyr Lys Val Asp Asn Ala Ala Asp Leu Ser Glu Ser
                405                 410                 415

Tyr Phe Val Asn Pro Glu Asn Phe Glu Asp Val Thr Asn Ser Val Asn
                420                 425                 430

Ile Thr Phe Pro Asn Pro Asn Gln Tyr Lys Val Glu Phe Asn Thr Pro
                435                 440                 445

Asp Asp Gln Ile Thr Thr Pro Tyr Ile Val Val Asn Gly His Ile
        450                     455                 460

Asp Pro Asn Ser Lys Gly Asp Leu Ala Leu Arg Ser Thr Leu Tyr Gly
465                     470                 475                 480

Tyr Asn Ser Asn Ile Ile Trp Arg Ser Met Ser Trp Asp Asn Glu Val
                485                 490                 495

Ala Phe Asn Asn Gly Ser Gly Ser Gly Asp Gly Ile Asp Lys Pro Val
                500                 505                 510
```

```
Val Pro Glu Gln Pro Asp Glu Pro Gly Glu Ile Glu Pro Ile Pro Glu
        515                 520                 525

Lys Leu
    530

<210> SEQ ID NO 9
<211> LENGTH: 339
<212> TYPE: PRT
<213> ORGANISM: ARTIFICIAL
<220> FEATURE:
<223> OTHER INFORMATION: rClfA residues 221-559

<400> SEQUENCE: 9

Val Ala Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
    50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Asp Val Lys Ala Thr
            100                 105                 110

Leu Thr Met Pro Ala Tyr Ile Asp Pro Glu Asn Val Lys Lys Thr Gly
        115                 120                 125

Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
    210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
    290                 295                 300

Asn Glu Val Ala Phe Asn Gly Ser Gly Ser Gly Asp Gly Ile Asp
305                 310                 315                 320

Lys Pro Val Val Pro Glu Gln Pro Asp Glu Pro Gly Glu Ile Glu Pro
                325                 330                 335
```

-continued

Ile Pro Glu

<210> SEQ ID NO 10
<211> LENGTH: 349
<212> TYPE: PRT
<213> ORGANISM: ARTIFICIAL
<220> FEATURE:
<223> OTHER INFORMATION: rClfA residues 221 to 559 with additional N and
      C terminal residues

<400> SEQUENCE: 10

```
His His His His His His Gly Ser Val Ala Ala Asp Ala Pro Ala Ala
1               5                   10                  15

Gly Thr Asp Ile Thr Asn Gln Leu Thr Asn Val Thr Val Gly Ile Asp
            20                  25                  30

Ser Gly Thr Thr Val Tyr Pro His Gln Ala Gly Tyr Val Lys Leu Asn
        35                  40                  45

Tyr Gly Phe Ser Val Pro Asn Ser Ala Val Lys Gly Asp Thr Phe Lys
    50                  55                  60

Ile Thr Val Pro Lys Glu Leu Asn Leu Asn Gly Val Thr Ser Thr Ala
65                  70                  75                  80

Lys Val Pro Pro Ile Met Ala Gly Asp Gln Val Leu Ala Asn Gly Val
                85                  90                  95

Ile Asp Ser Asp Gly Asn Val Ile Tyr Thr Phe Thr Asp Tyr Val Asn
            100                 105                 110

Thr Lys Asp Asp Val Lys Ala Thr Leu Thr Met Pro Ala Tyr Ile Asp
        115                 120                 125

Pro Glu Asn Val Lys Lys Thr Gly Asn Val Thr Leu Ala Thr Gly Ile
    130                 135                 140

Gly Ser Thr Thr Ala Asn Lys Thr Val Leu Val Asp Tyr Glu Lys Tyr
145                 150                 155                 160

Gly Lys Phe Tyr Asn Leu Ser Ile Lys Gly Thr Ile Asp Gln Ile Asp
                165                 170                 175

Lys Thr Asn Asn Thr Tyr Arg Gln Thr Ile Tyr Val Asn Pro Ser Gly
            180                 185                 190

Asp Asn Val Ile Ala Pro Val Leu Thr Gly Asn Leu Lys Pro Asn Thr
        195                 200                 205

Asp Ser Asn Ala Leu Ile Asp Gln Gln Asn Thr Ser Ile Lys Val Tyr
    210                 215                 220

Lys Val Asp Asn Ala Ala Asp Leu Ser Glu Ser Tyr Phe Val Asn Pro
225                 230                 235                 240

Glu Asn Phe Glu Asp Val Thr Asn Ser Val Asn Ile Thr Phe Pro Asn
                245                 250                 255

Pro Asn Gln Tyr Lys Val Glu Phe Asn Thr Pro Asp Asp Gln Ile Thr
            260                 265                 270

Thr Pro Tyr Ile Val Val Asn Gly His Ile Asp Pro Asn Ser Lys
        275                 280                 285

Gly Asp Leu Ala Leu Arg Ser Thr Leu Tyr Gly Tyr Asn Ser Asn Ile
    290                 295                 300

Ile Trp Arg Ser Met Ser Trp Asp Asn Glu Val Ala Phe Asn Asn Gly
305                 310                 315                 320

Ser Gly Ser Gly Asp Gly Ile Asp Lys Pro Val Val Pro Glu Gln Pro
                325                 330                 335

Asp Glu Pro Gly Glu Ile Glu Pro Ile Pro Glu Lys Leu
            340                 345
```

<210> SEQ ID NO 11
<211> LENGTH: 339
<212> TYPE: PRT
<213> ORGANISM: ARTIFICIAL
<220> FEATURE:
<223> OTHER INFORMATION: rClfA PY 221 to 559

<400> SEQUENCE: 11

Val Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
                20                  25                  30

Gln Ala Gly Tyr Val Lys Leu Asn Tyr Gly Phe Ser Val Pro Asn Ser
            35                  40                  45

Ala Val Lys Gly Asp Thr Phe Lys Ile Thr Val Pro Lys Glu Leu Asn
        50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Asp Val Lys Ala Thr
            100                 105                 110

Leu Thr Met Ser Ala Ala Ile Asp Pro Glu Asn Val Lys Lys Thr Gly
        115                 120                 125

Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
    210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
    290                 295                 300

Asn Glu Val Ala Phe Asn Asn Gly Ser Gly Ser Gly Asp Gly Ile Asp
305                 310                 315                 320

Lys Pro Val Val Pro Glu Gln Pro Asp Glu Pro Gly Glu Ile Glu Pro
                325                 330                 335

Ile Pro Glu

<210> SEQ ID NO 12
<211> LENGTH: 349

<212> TYPE: PRT
<213> ORGANISM: ARTIFICIAL
<220> FEATURE:
<223> OTHER INFORMATION: rClfA PY 221 to 559 with additional N and C
      terminal residues

<400> SEQUENCE: 12

His His His His His Gly Ser Val Ala Asp Ala Pro Ala
1               5                   10                  15

Gly Thr Asp Ile Thr Asn Gln Leu Thr Asn Val Thr Val Gly Ile Asp
            20                  25                  30

Ser Gly Thr Thr Val Tyr Pro His Gln Ala Gly Tyr Val Lys Leu Asn
        35                  40                  45

Tyr Gly Phe Ser Val Pro Asn Ser Ala Val Lys Gly Asp Thr Phe Lys
    50                  55                  60

Ile Thr Val Pro Lys Glu Leu Asn Leu Asn Gly Val Thr Ser Thr Ala
65                  70                  75                  80

Lys Val Pro Pro Ile Met Ala Gly Asp Gln Val Leu Ala Asn Gly Val
                85                  90                  95

Ile Asp Ser Asp Gly Asn Val Ile Tyr Thr Phe Thr Asp Tyr Val Asn
            100                 105                 110

Thr Lys Asp Asp Val Lys Ala Thr Leu Thr Met Ser Ala Ala Ile Asp
        115                 120                 125

Pro Glu Asn Val Lys Lys Thr Gly Asn Val Thr Leu Ala Thr Gly Ile
    130                 135                 140

Gly Ser Thr Thr Ala Asn Lys Thr Val Leu Val Asp Tyr Glu Lys Tyr
145                 150                 155                 160

Gly Lys Phe Tyr Asn Leu Ser Ile Lys Gly Thr Ile Asp Gln Ile Asp
                165                 170                 175

Lys Thr Asn Asn Thr Tyr Arg Gln Thr Ile Tyr Val Asn Pro Ser Gly
            180                 185                 190

Asp Asn Val Ile Ala Pro Val Leu Thr Gly Asn Leu Lys Pro Asn Thr
        195                 200                 205

Asp Ser Asn Ala Leu Ile Asp Gln Gln Asn Thr Ser Ile Lys Val Tyr
    210                 215                 220

Lys Val Asp Asn Ala Ala Asp Leu Ser Glu Ser Tyr Phe Val Asn Pro
225                 230                 235                 240

Glu Asn Phe Glu Asp Val Thr Asn Ser Val Asn Ile Thr Phe Pro Asn
                245                 250                 255

Pro Asn Gln Tyr Lys Val Glu Phe Asn Thr Pro Asp Asp Gln Ile Thr
            260                 265                 270

Thr Pro Tyr Ile Val Val Val Asn Gly His Ile Asp Pro Asn Ser Lys
        275                 280                 285

Gly Asp Leu Ala Leu Arg Ser Thr Leu Tyr Gly Tyr Asn Ser Asn Ile
    290                 295                 300

Ile Trp Arg Ser Met Ser Trp Asp Asn Glu Val Ala Phe Asn Asn Gly
305                 310                 315                 320

Ser Gly Ser Gly Asp Gly Ile Asp Lys Pro Val Val Pro Glu Gln Pro
                325                 330                 335

Asp Glu Pro Gly Glu Ile Glu Pro Ile Pro Glu Lys Leu
            340                 345

<210> SEQ ID NO 13
<211> LENGTH: 321
<212> TYPE: PRT
<213> ORGANISM: ARTIFICIAL

<220> FEATURE:
<223> OTHER INFORMATION: rClfA residues 221 to 531 with additional N and
      C terminal residues (delta latch truncate)

<400> SEQUENCE: 13

His His His His His His Gly Ser Val Ala Ala Asp Ala Pro Ala Ala
1               5                   10                  15

Gly Thr Asp Ile Thr Asn Gln Leu Thr Asn Val Thr Val Gly Ile Asp
            20                  25                  30

Ser Gly Thr Thr Val Tyr Pro His Gln Ala Gly Tyr Val Lys Leu Asn
        35                  40                  45

Tyr Gly Phe Ser Val Pro Asn Ser Ala Val Lys Gly Asp Thr Phe Lys
50                  55                  60

Ile Thr Val Pro Lys Glu Leu Asn Leu Asn Gly Val Thr Ser Thr Ala
65                  70                  75                  80

Lys Val Pro Pro Ile Met Ala Gly Asp Gln Val Leu Ala Asn Gly Val
                85                  90                  95

Ile Asp Ser Asp Gly Asn Val Ile Tyr Thr Phe Thr Asp Tyr Val Asn
            100                 105                 110

Thr Lys Asp Asp Val Lys Ala Thr Leu Thr Met Pro Ala Tyr Ile Asp
        115                 120                 125

Pro Glu Asn Val Lys Lys Thr Gly Asn Val Thr Leu Ala Thr Gly Ile
    130                 135                 140

Gly Ser Thr Thr Ala Asn Lys Thr Val Leu Val Asp Tyr Glu Lys Tyr
145                 150                 155                 160

Gly Lys Phe Tyr Asn Leu Ser Ile Lys Gly Thr Ile Asp Gln Ile Asp
                165                 170                 175

Lys Thr Asn Asn Thr Tyr Arg Gln Thr Ile Tyr Val Asn Pro Ser Gly
            180                 185                 190

Asp Asn Val Ile Ala Pro Val Leu Thr Gly Asn Leu Lys Pro Asn Thr
        195                 200                 205

Asp Ser Asn Ala Leu Ile Asp Gln Gln Asn Thr Ser Ile Lys Val Tyr
    210                 215                 220

Lys Val Asp Asn Ala Ala Asp Leu Ser Glu Ser Tyr Phe Val Asn Pro
225                 230                 235                 240

Glu Asn Phe Glu Asp Val Thr Asn Ser Val Asn Ile Thr Phe Pro Asn
                245                 250                 255

Pro Asn Gln Tyr Lys Val Glu Phe Asn Thr Pro Asp Asp Gln Ile Thr
            260                 265                 270

Thr Pro Tyr Ile Val Val Asn Gly His Ile Asp Pro Asn Ser Lys
        275                 280                 285

Gly Asp Leu Ala Leu Arg Ser Thr Leu Tyr Gly Tyr Asn Ser Asn Ile
    290                 295                 300

Ile Trp Arg Ser Met Ser Trp Asp Asn Glu Val Ala Phe Asn Asn Arg
305                 310                 315                 320

Ser

<210> SEQ ID NO 14
<211> LENGTH: 311
<212> TYPE: PRT
<213> ORGANISM: ARTIFICIAL
<220> FEATURE:
<223> OTHER INFORMATION: rClfA residues 221 to 531 (delta latch
      truncate)

<400> SEQUENCE: 14

-continued

| | | | | | | | | | | | | | | |
|---|---|---|---|---|---|---|---|---|---|---|---|---|---|---|
| Val<br>1 | Ala | Ala | Asp | Ala<br>5 | Pro | Ala | Ala | Gly | Thr<br>10 | Asp | Ile | Thr | Asn | Gln<br>15 | Leu |
| Thr | Asn | Val | Thr<br>20 | Val | Gly | Ile | Asp | Ser<br>25 | Gly | Thr | Thr | Val | Tyr<br>30 | Pro | His |
| Gln | Ala | Gly<br>35 | Tyr | Val | Lys | Leu | Asn<br>40 | Tyr | Gly | Phe | Ser | Val<br>45 | Pro | Asn | Ser |
| Ala | Val<br>50 | Lys | Gly | Asp | Thr | Phe<br>55 | Lys | Ile | Thr | Val | Pro<br>60 | Lys | Glu | Leu | Asn |
| Leu<br>65 | Asn | Gly | Val | Thr | Ser<br>70 | Thr | Ala | Lys | Val | Pro<br>75 | Ile | Met | Ala | Gly<br>80 | |
| Asp | Gln | Val | Leu | Ala<br>85 | Asn | Gly | Val | Ile | Asp<br>90 | Ser | Asp | Gly | Asn | Val<br>95 | Ile |
| Tyr | Thr | Phe | Thr<br>100 | Asp | Tyr | Val | Asn | Thr<br>105 | Lys | Asp | Asp | Val | Lys<br>110 | Ala | Thr |
| Leu | Thr | Met<br>115 | Pro | Ala | Tyr | Ile | Asp<br>120 | Pro | Glu | Asn | Val | Lys<br>125 | Lys | Thr | Gly |
| Asn | Val<br>130 | Thr | Leu | Ala | Thr | Gly<br>135 | Ile | Gly | Ser | Thr | Thr<br>140 | Ala | Asn | Lys | Thr |
| Val<br>145 | Leu | Val | Asp | Tyr | Glu<br>150 | Lys | Tyr | Gly | Lys | Phe<br>155 | Tyr | Asn | Leu | Ser | Ile<br>160 |
| Lys | Gly | Thr | Ile | Asp<br>165 | Gln | Ile | Asp | Lys | Thr<br>170 | Asn | Asn | Thr | Tyr | Arg<br>175 | Gln |
| Thr | Ile | Tyr | Val<br>180 | Asn | Pro | Ser | Gly | Asp<br>185 | Asn | Val | Ile | Ala | Pro<br>190 | Val | Leu |
| Thr | Gly | Asn<br>195 | Leu | Lys | Pro | Asn | Thr<br>200 | Asp | Ser | Asn | Ala | Leu<br>205 | Ile | Asp | Gln |
| Gln | Asn<br>210 | Thr | Ser | Ile | Lys | Val<br>215 | Tyr | Lys | Val | Asp | Asn<br>220 | Ala | Ala | Asp | Leu |
| Ser<br>225 | Glu | Ser | Tyr | Phe | Val<br>230 | Asn | Pro | Glu | Asn | Phe<br>235 | Glu | Asp | Val | Thr | Asn<br>240 |
| Ser | Val | Asn | Ile | Thr<br>245 | Phe | Pro | Asn | Pro | Asn<br>250 | Gln | Tyr | Lys | Val | Glu<br>255 | Phe |
| Asn | Thr | Pro | Asp<br>260 | Asp | Gln | Ile | Thr | Thr<br>265 | Pro | Tyr | Ile | Val | Val<br>270 | Val | Asn |
| Gly | His | Ile | Asp<br>275 | Pro | Asn | Ser | Lys<br>280 | Gly | Asp | Leu | Ala | Leu<br>285 | Arg | Ser | Thr |
| Leu | Tyr<br>290 | Gly | Tyr | Asn | Ser | Asn<br>295 | Ile | Ile | Trp | Arg | Ser<br>300 | Met | Ser | Trp | Asp |
| Asn<br>305 | Glu | Val | Ala | Phe | Asn<br>310 | Asn | | | | | | | | | |

The invention claimed is:

1. A method of inducing an immune response in an individual comprising the steps of administering to the individual an effective amount of a recombinant staphylococcal clumping factor A (ClfA) or fragment thereof comprising at least amino acid residues 221 to 531 of the fibrinogen binding region (Region A), characterized by at least one amino acid residue substitution or deletion at amino acid residue Ala254, Tyr256, Pro336, Tyr338, Ile387, Lys389, Glu526 and/or Val527 to result in a recombinant fibrinogen binding protein with reduced ability or lacking the ability to non-covalently bind fibrinogen; and st 4. The method according to claim 2, wherein the recombinant staphylococcal clumping factor A (ClfA) comprises two DEv-IgG domains forming a hydrophobic pocket wherein
the hydrophobic pocket formed between the two DEv-IgG domains is altered to reduce or prevent fibrinogen binding; or
the fibrinogen binding protein comprises a latching peptide which covers the fibrinogen in the hydrophobic trench and the latching peptide is altered or removed to reduce or prevent fibrinogen binding.

5. The method according to claim 2, wherein the recombinant staphylococcal clumping factor A (ClfA) comprises the fibrinogen binding region only or a fragment thereof.

6. The method according to claim 2, wherein the recombinant staphylococcal clumping factor A (ClfA) is derived from *S. aureus, S. epidermidis* and/or *S. lugdunensis*.

7. The method according to claim 2, wherein the recombinant staphylococcal clumping factor A (ClfA) comprises the fibrinogen binding Region A of the fibrinogen binding protein wherein the amino acid substitution or deletion reduces the non-covalent interaction with fibrinogen.

8. The method according to claim 7, wherein the reduction of non-covalent interaction is by preventing or reducing ligand binding to the hydrophobic pocket separating Region A subregions N2 and N3 of the fibrinogen binding protein.

9. The method according to claim 2, wherein the recombinant staphylococcal clumping factor A (ClfA) comprises the fibrinogen binding region without the latching peptide amino acid residues to result in a recombinant fibrinogen binding protein with reduced ability or lacking the ability to non-covalently bind fibrinogen.

10. The method according to claim 2, wherein the recombinant staphylococcal clumping factor A (ClfA) amino acid residues Ala254, Tyr256, Pro336, Tyr338, Ile387, Lys389, Glu526 and/or Val527 are substituted with either Ala or Ser.

11. The method according to claim 2, wherein residue $P_{336}$ and/or $Y_{338}$ of the fibrinogen binding region (Region A) of ClfA is substituted with either serine or alanine to result in rClfA$P_{336}$S $Y_{338}$A or rClfA$P_{336}$A $Y_{338}$S.

12. The method according to claim 2, wherein the recombinant staphylococcal clumping factor A (ClfA) fibrinogen binding protein has the amino acid sequence according to any of SEQ ID Nos. 1 to 3 wherein residue $P_{336}$ and/or $Y_{338}$ are substituted with either serine and/or alanine, or fragment thereof.

13. The method according to claim 2, wherein the recombinant staphylococcal clumping factor A (ClfA) comprises the fibrinogen binding protein, the fibrinogen binding region, the minimal fibrinogen binding region and/or a fragment thereof.

14. The method according to claim 2, wherein the recombinant staphylococcal clumping factor A (ClfA) fragment comprises at least part of the fibrinogen binding region to result in a recombinant fragment of the fibrinogen binding protein with reduced ability or lacking the ability to non-covalently bind fibrinogen.

15. The method according to claim 2, wherein the recombinant staphylococcal clumping factor A (ClfA) comprises
a. Subregions N1, N2 and N3, spanning amino acid residues 40 to 559 of the fibrinogen binding region (Region A);
b. Subregions N2 and N3, spanning amino acid residues 221 to 559 of the fibrinogen binding region of ClfA (Region A); and/or
c. Amino acid residues 221 to 531 of the fibrinogen binding region (Region A).

16. The method according to claim 2, wherein the recombinant staphylococcal clumping factor A (ClfA) comprises the amino acid sequence according to any of SEQ ID Nos. 4 to 14.

17. The method according to claim 2, for the treatment or prophylaxis of staphylococcal infections, including sepsis, septic arthritis and/or endocarditis.

18. The method according to claim 2, wherein the infection is a *Staphylococcus aureus* infection.

19. The method according to claim 2, wherein the ClfA or fragment thereof comprises at least one amino acid residue substitution at amino acid residues Tyr256, Pro336, Tyr338, Lys389, Glu526 and/or Val527.

* * * * *